US012643907B2

(12) United States Patent
Katritch et al.

(10) Patent No.: US 12,643,907 B2
(45) Date of Patent: Jun. 2, 2026

(54) OPIOID RECEPTOR ANTAGONISTS

(71) Applicant: UNIVERSITY OF SOUTHERN CALIFORNIA, Los Angeles, CA (US)

(72) Inventors: Vsevolod Katritch, Los Angeles, CA (US); Valery V. Fokin, Los Angeles, CA (US); Saheem Zaidi, Los Angeles, CA (US); Joice Thomas, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 832 days.

(21) Appl. No.: 17/908,203

(22) PCT Filed: Mar. 2, 2021

(86) PCT No.: PCT/US2021/020469

§ 371 (c)(1),
(2) Date: Aug. 30, 2022

(87) PCT Pub. No.: WO2021/178405

PCT Pub. Date: Sep. 10, 2021

(65) Prior Publication Data

US 2023/0111856 A1 Apr. 13, 2023

Related U.S. Application Data

(60) Provisional application No. 62/984,126, filed on Mar. 2, 2020.

(51) Int. Cl.
*C07D 489/08* (2006.01)
*A61P 11/16* (2006.01)

(52) U.S. Cl.
CPC ............ *C07D 489/08* (2013.01); *A61P 11/16* (2018.01)

(58) Field of Classification Search
CPC .................................................... C07D 489/08
See application file for complete search history.

(56) References Cited

U.S. PATENT DOCUMENTS

| | | | |
|---|---|---|---|
| 6,177,438 B1 | 1/2001 | Nagase et al. |
| 10,117,840 B2 | 11/2018 | Dong et al. |
| 2010/0240691 A1 | 9/2010 | Turncliff et al. |
| 2011/0263630 A1 | 10/2011 | Cashman |

OTHER PUBLICATIONS

American Chemical Society. Chemical Abstract Service. RN 1839621-14-5. Entered into STN: Dec. 31, 2015. (Year: 2015).*
Chen et al., "Arylfluorosulfates Inactivate Intracellular Lipid Binding Protein(s) Through Chemoselective SuFEx Reaction with a Binding Site Tyr Residue," J Am Chem Soc., 138(23):7353-7364, May 2016.
International Search Report and Written Opinion of the ISA/US in PCT/US2021/020469, dated May 21, 2021; 8pgs.
Khroyan et al., "In Vitro and In Vivo Profile of PPI-101 and PPI-103: Mixed Opioid Partial Agonist Analgesics with Low Abuse Potential," Front Psychiatry, 8(52);1-15, Apr. 2017.
Mclaughlin et al., "Prolonged Kappa Opioid Receptor Phosphorylation Mediated by G-protein Receptor Kinase Underlies Sustained Analgesic Tolerance," J Biol Chem., 279(3):1810-1818, Jan. 2004.
Mohamed et al., "Activity of N-methyl-.Alpha.- and -.Beta.-Funaltrexamine at Opioid Receptors," J Med Chem., 29(8):1551-1553, Aug. 1986.
Ohno et al., "Solid-Phase Synthesis of 6-Sulfonylamino Morphinan Libraries," Synlett, 1:93-96, Dec. 2002.
PubChem, SCHEMBL14161012, Compound CID: 89265121, "(1R,9R,10S)-10-amino-17-(cyclopropylmethyl)-3-hydroxy-4-methoxy-17-azatetracyclo[7.5.3.01,10.02,7]heptadeca-2(7),3,5-trien-13-one,".
PubChem, SCHEMBL18529739, Compound CID: 126601618 "(4R,4aS,7aR,12bS)-3-(cyclopropylmethyl)-4a-fluorosulfonyloxy-9-hydroxy-7-oxo-2,4,5,6,7a,13-hexahydro-1H-4,12-methanobenzofuro[3,2-e]isoquinoline,".
PubChem, SCHEMBL18529767, Compound CID: 126601646, "(4R,4aS,7aR,12bS)-3-(cyclopropylmethyl)-9-hydroxy-7-oxo-2,4,5,6,7a,13-hexahydro-1H-4,12-methanobenzofuro[3,2-e]isoquinoline-4a-sulfonyl fluoride,".

* cited by examiner

*Primary Examiner* — John S Kenyon
(74) *Attorney, Agent, or Firm* — Haukaas Fortius PLLC; Michael H. Haukaas; Raymond F. Horvath

(57) ABSTRACT

The first selective SuFEx antagonists to μ-opioid receptors (MOR) were developed by functionalizing an opioid scaffold with an $SO_2$—F warhead. Our model, based on a MOR structure with antagonist β-FNA, indicates the naloxone carbonyl as an advantageous point for derivatization as it is chemically accessible and is not involved in interaction with receptors. Of the three accessible Tyr residues in MOR pocket, Tyr77, Tyr130 and Tyr150, Tyr150 in proximity to the carbonyl of the docked naloxone was selected as a target, which resulted in the development of highly potent antagonists.

18 Claims, 8 Drawing Sheets

(A)

(B)

(A)

(B)

(A)

(B)

(A)

(B)

OPIOID RECEPTOR ANTAGONISTS

RELATED APPLICATIONS

This application is a National Stage filing under 35 U.S.C. § 371 of International Application No. PCT/US2021/020469 filed Mar. 2, 2021, which claims the benefit of U.S. Provisional Patent Application No. 62/984,126 filed Mar. 2, 2020, which applications are incorporated herein by reference.

BACKGROUND OF THE INVENTION

Fentanyl is an FDA approved synthetic opioid analgesic with a potency 50-100 times greater than morphine and a half-life of 7-8 hours. While it is widely used in general anesthesia, treatment of cancer pain, and palliative care, fentanyl has a very narrow therapeutic window. The lethal dose for an adult human estimated at ~2 mg; the lethal dose of some derivatives is even less. Illicit fentanyl use has exploded in the past few years, transforming the nature of the opioid epidemic in the United States. Fentanyl is considered the deadliest toxin in the U.S. and has become the leading cause of opioid overdose-related deaths, with 31,800 deaths in 2018 (a 20-fold increase since 2011).

The current standard for treating opioid overdose is naloxone, which is an antagonist of the μ-opioid receptor (MOR). Unfortunately, naloxone has modest potency compared to fentanyl and a vastly disadvantaged 2-hour half-life, resulting in lethal outcomes even when proper emergency procedures are followed. Patients who have overdosed on fentanyl can re-narcotize after an initial administration of naloxone. The deficiencies of naloxone are further highlighted by recent statistics showing that while the rate of lethal overdose for traditional opioids has stabilized, the death rate for fentanyl and its derivatives is rapidly rising. To combat the growing use of fentanyl and its derivatives, a reversal agent that can address the potency and PK properties of fentanyl is urgently needed.

A potent, long-lasting, covalently binding MOR antagonist would be a transformative new approach to treat fentanyl overdose. The duration of action of irreversible MOR antagonism is sustainable and corresponds to the rate of endogenous MOR turnover, which in the primates is about six days. The potential utility of an irreversible MOR antagonist was shown by studying the covalently binding antagonist β-funaltrexamine (β-FNA), which proved effective in blocking opioid self-administration in nonhuman subjects. The long-lasting, pseudo-irreversible MOR antagonists clocinnamox (C-CAM) and methocinnamox (M-CAM) were found safe and effective for treating opioid abuse and reversing heroin overdose, with sustainable effects implying MOR blockade lasting for several days. A crystal structure of β-FNA in complex with MOR was also described, which validated its covalent binding. A few morphinan-based covalent antagonists are currently available but have chemical or functional properties restricting their clinical use. For example, the dihydromorphine derivative $H_2$BAM covalently labels the MOR only under alkaline conditions, which precludes its use in vivo. Moreover, both β-FNA and dihydrocodeinone derivative N-CPM-CACO have unwanted opioid agonist properties, requiring a 24 hour delay after administration for useful MOR-selective antagonism.

Accordingly, there is a need for safe and longer acting treatments for subjects suffering from opioid overdoses.

SUMMARY

Potent and selective covalent MOR antagonists were designed based on highly selective bioorthogonal proximity-guided click chemistry using SuFEx reactions. Unlike other well-studied electrophilic warheads used for protein modification (such as fluorophosphonates, vinyl sulfones, and acrylamides), the SuFEx reaction uses sulfur(VI)-fluoride functional groups such as alkyl-$SO_2F$ and aryl-O—$SO_2F$ to react with phenol group of Tyr side chains (FIG. 1).

In contrast to previous warheads, these SuFEx functional groups are exceedingly weak electrophiles that require very tight protein binding and accurate reactant positioning to become reactive. Therefore, selective MOR ligands functionalized with a SuFEx warhead, and capable of positioning this warhead precisely at a selected Tyr side chain in MOR binding pocket, ensures covalent bonding exclusively to MOR. Such covalent binding can be highly receptor-selective and can bind to targeted intracellular proteins without substantial interference from other cell components, thus demonstrating utility in therapeutic applications.

The invention provides selective SuFEx antagonists of MOR for prolonged protection and reversal of severe overdose with fentanyl and other synthetic opioids. The results described herein indicate that the structure-based rational design of SuFEx functionalized ligands can be effectively used as irreversible blockers of MOR. This is achieved by functionalizing known selective opioid antagonist scaffolds (e.g., naloxone, cyprodime, or samidorphan) with a SuFEx warhead. Because the rate of the reaction is exceptionally sensitive to the proximity of the nucleophile, the SuFEx ligands described herein were designed to position the reactive $SO_2$—F warhead such that it is directly attacked by the phenolic oxygen of the Tyr150 in the opioid receptor target pocket. The availability of structural information recently generated for opioid receptors, including MOR, KOR, and DOR, as well as the computer-assisted structure-based ligand discovery platforms was key to development of this new technology platform.

In vitro tests for the rationally designed SuFEx lead prototype TJ-345 and its individual stereoisomers showed irreversible MOR inhibition and blocking of agonist-induced activation. Importantly, in vivo results in mice have already demonstrated that TJ-345 completely blocks morphine activity for more than 48 hours upon intracerebroventricular (i.c.v.) delivery as compared to <3 hours for naloxone. Moreover, TJ-345 is also effective in a blockade of fentanyl-induced respiratory depression after subcutaneous (s.c.) delivery, indicating promising PK properties and acceptable brain exposure.

Accordingly, the invention provides compounds that are a mu-opioid antagonists comprising a sulfur(VI) fluoride group wherein the antagonist covalently binds to a mu-opioid receptor via the sulfur(VI) fluoride group when the antagonist is in contact with the mu-opioid receptor. In various embodiments, the antagonist is a compound of Formula I.

(I)

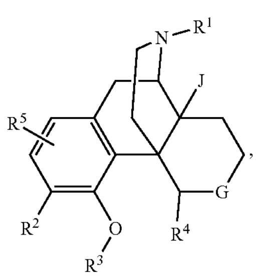
, or a stereoisomer thereof;

wherein

G is C═O, $CHR^x$, $CHOR^a$, or $CHNR^bR^c$; wherein $R^x$ is H or —($C_1$-$C_8$)alkyl; $R^a$ is H, —($C_1$-$C_8$)alkyl, or —($C_1$-$C_8$)cycloalkyl; $R^b$ and $R^c$ are each independently H, —($C_1$-$C_8$)alkyl, —($C_1$-$C_8$)cycloalkyl, —C(═O)$R^d$, or —S(═O)$_2R^e$; wherein $R^d$ or $R^e$ is —($C_1$-$C_8$)alkyl, —($C_3$-$C_8$)cycloalkyl, or phenyl, wherein —($C_1$-$C_8$) alkyl, —($C_3$-$C_8$)cycloalkyl, or phenyl is substituted with —S(═O)$_2$F or unsaturated or saturated —($C_1$-$C_8$) alkyl-S(═O)$_2$F;

J is H, $OR^a$, $NR^bR^c$, or J and G taken together form an alkyl bridge;

$R^1$ is H, —($C_1$-$C_8$)alkyl, —($C_1$-$C_8$)cycloalkyl, —C(═O) $R^d$, or —S(═O)$_2R^e$;

$R^2$ is H, $OR^f$, —($C_0$-$C_5$)C(═O)$R^f$, —($C_0$-$C_5$)C(═O)O$R^f$, —($C_0$-$C_5$)OC(═O)O$R^f$, wherein $R^f$ is —($C_1$-$C_8$)alkyl wherein —($C_1$-$C_8$)alkyl is substituted optionally with amine;

$R^3$ is H, —($C_1$-$C_8$)alkyl, or —($C_1$-$C_8$)cycloalkyl;

$R^4$ is H or $R^3$ and $R^4$ taken together form a single bond; and $R^5$ is H, halo, or —($C_1$-$C_8$)alkyl;

wherein —($C_1$-$C_8$)alkyl is unsaturated or saturated and unbranched or branched, —($C_1$-$C_8$)cycloalkyl comprises an optional ring heteroatom, and at least of one of J, G, or $R^1$ comprises —S(═O)$_2$F.

The invention also provides a method to treat an opioid drug overdose comprising administering a mu-opioid antagonist compound of a formula described herein, such as Formula I, II, IIA, IIB, IIC, III, or IIIA, to a subject in need thereof, wherein the antagonist covalently binds to the subject's mu-opioid receptors via the sulfur(VI) fluoride group when the antagonist is in contact with the mu-opioid receptors, thereby treating the drug overdose. In some embodiments, the compound can be used to treat opioid use disorder and/or opioid addiction. In some embodiments, the antagonist is TJ-345:

(TJ-345)

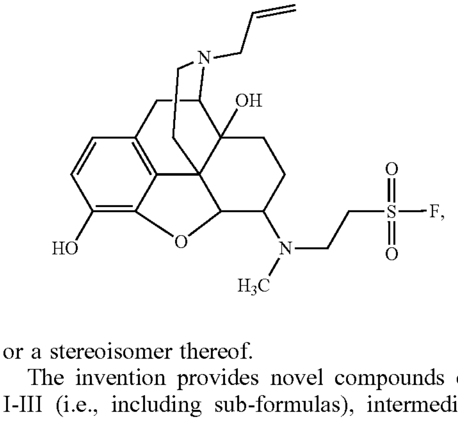

or a stereoisomer thereof.

The invention provides novel compounds of Formulas I-III (i.e., including sub-formulas), intermediates for the synthesis of compounds of Formulas I-III, as well as methods of preparing compounds of Formulas I-III. The invention also provides compounds of Formulas I-III that are useful as intermediates for the synthesis of other useful compounds. The invention provides for the use of compounds of Formulas I-III for the manufacture of medicaments useful for the treatment of opioid overdoses in a mammal, such as a human.

The invention provides for the use of the compositions described herein for use in medical therapy. The medical therapy can be treating opioid overdoses. The invention also provides for the use of a composition as described herein for the manufacture of a medicament to treat a disease in a mammal, for example, opioid addiction or opioid overdose in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
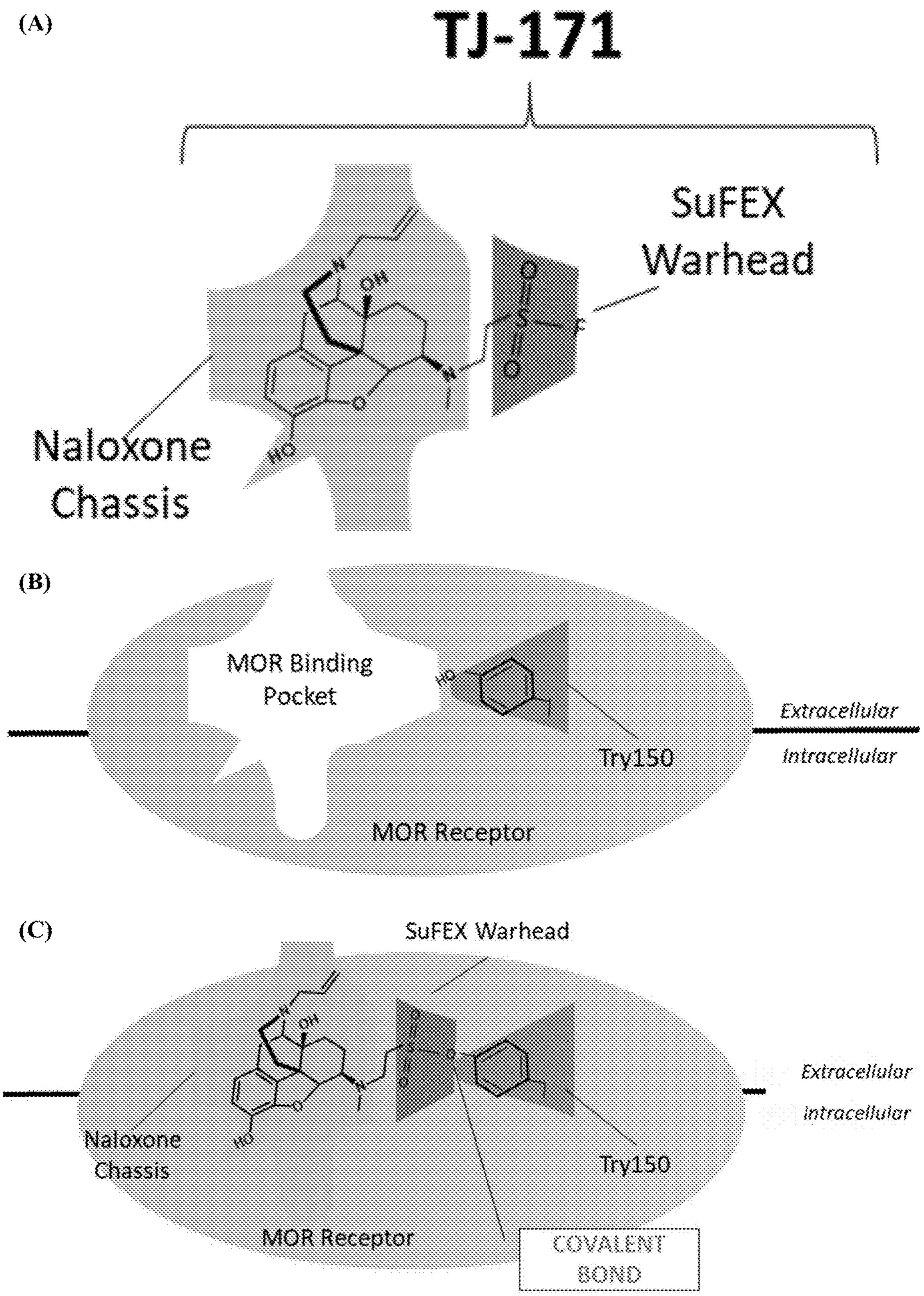
FIG. 1. The SuFEX lead compound TJ-171 selective to MOR. (A) Schematic of the TJ-171 naloxone 'chassis' with SuFEX 'warhead'. (B) MOR binding pocket with exposed phenol of Try150. (C) Bioorthogonal click chemistry SuFEX reaction between TJ-171 and exposed phenol of Try150 to form a covalent bond.

The opiate crisis in America has reached epidemic proportions. In 2018 alone there were 47,500 deaths from opiate overdose with 31,900 of them caused by the highly potent synthetic opioid fentanyl and fentanyl-related compounds.

Naloxone is the most widely used antagonist to treat acute opiate overdose. However, the fast off-rate and short half-life make it insufficient to overcome the sub-nanomolar affinity and long half-life of fentanyl and derivatives. In fact, respiratory depression, coma, and death induced by highly potent MOR agonists like fentanyl occur even after proper emergency treatment and procedures have been administered. Covalent irreversible antagonists of MOR can be more effective in achieving higher potency prolonged blockade of fentanyl, thus improving patient survival. Some known covalent antagonists like β-FNA have shown proof of principle by effectively and sustainably blocking opioid effects in vitro and in vivo in nonhuman subjects. However, β-FNA and other known covalent antagonists are based on chemistries that are not selective in vivo, precluding their use in humans.

Innovative bioorthogonal chemistry was used to develop highly selective, irreversible μ-Opioid Receptor (MOR) antagonists. These highly potent and long-lasting opioid antagonists can be used as reversal agents to treat acute opiate overdose.

The highly selective and safe covalent antagonists were developed using a technique referred to as bioorthogonal proximity-guided click chemistry. Specifically, the Sulfur (VI) Fluoride Exchange (SuFEx) reaction was utilized by linking a sulfonyl fluoride ($SO_2F$) moiety to naloxone. By "functionalizing" a known selective MOR antagonist with a weak electrophilic "warhead" capable of forming covalent bonds, we have engineered a novel, selective, and safe covalent binding drug. The naloxone moiety selectively recognizes the MOR, precisely positioning the $SO_2F$ warhead to form a covalent bond to an exposed phenol group of the tyrosine side chain in the binding pocket.

One example of the drug is TJ-345, which shows high MOR affinity ($K_i$=15 nM) and efficient irreversible in vitro MOR antagonism. In vivo efficacy tests of TJ-345 demonstrate long-lasting (>24-48 hour) blockade of opiate analgesia at doses as low as 3 nmol (i.c.v), or 30 mg/kg, (s.c.), as well as reversal of fentanyl-induced respiratory depression by 30 mg/kg TJ-345 (s.c.).

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, as well as 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', $OC(O)N(R')_2$, CN, $CF_3$, $OCF_3$, R', O, S, C(O), S(O), methylenedioxy, ethylenedioxy, $N(R')_2$, SR', SOR', $SO_2R'$, $SO_2N(R')_2$, $SO_3R'$, C(O)R', C(O)C(O)R', $C(O)CH_2C(O)R'$, C(S)R', C(O)OR', OC(O)R', $C(O)N(R')_2$, $OC(O)N(R')_2$, $C(S)N(R')_2$, $(CH_2)_{0-2}NHC(O)R'$, N(R')N(R')C(O)R', N(R')N(R')C(O)OR', $N(R')N(R')CON(R')_2$, $N(R')SO_2R'$, $N(R')SO_2N(R')_2$, N(R')C(O)OR', N(R')C(O)R', N(R')C(S)R', $N(R')C(O)N(R')_2$, $N(R')C(S)N(R')_2$, N(COR')COR', N(OR')R', $C(=NH)N(R')_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or $S(O)_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as in 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1\text{-}C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof, such as racemic mixtures, which form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate (defined below), which may occur where there has been no stereoselection or stereospecificity in a chemical reaction or process.

The terms "racemic mixture" and "racemate" refer to an equimolar mixture of two enantiomeric species, devoid of optical activity.

The term "enantiomerically enriched" ("ee") as used herein refers to mixtures that have one enantiomer present to a greater extent than another. Reactions that provide one enantiomer present to a greater extent than another would therefore be "enantioselective" (or demonstrate "enantioselectivity").

Embodiments of the Invention

This invention provides organic compounds that are a mu-opioid antagonist comprising a sulfur (VI) fluoride group wherein the antagonist covalently binds to a mu-opioid receptor via the sulfur (VI) fluoride group when the antagonist is in contact with the mu-opioid receptor.

In various embodiments, the mu-opioid antagonist is a compound of Formula I:

(I)

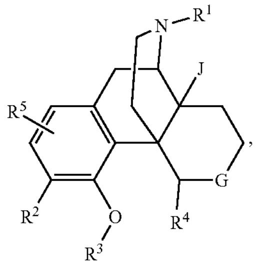

or a stereoisomer thereof;

wherein

- G is C═O, $CHR^x$, $CHOR^a$, or $CHNR^bR^c$; wherein $R^x$ is H or —$(C_1\text{-}C_8)$alkyl; $R^a$ is H, —$(C_1\text{-}C_8)$alkyl, or —$(C_1\text{-}C_8)$cycloalkyl; $R^b$ and $R^c$ are each independently H, —$(C_1\text{-}C_8)$alkyl, —$(C_1\text{-}C_8)$cycloalkyl, —C(═O)$R^d$, or —S(═O)$_2R^e$; wherein $R^d$ or $R^e$ is —$(C_1\text{-}C_8)$alkyl, —$(C_3\text{-}C_8)$cycloalkyl, or phenyl, wherein —$(C_1\text{-}C_8)$alkyl, —$(C_3\text{-}C_8)$cycloalkyl, or phenyl is substituted with —S(═O)$_2$F or unsaturated or saturated —$(C_1\text{-}C_8)$alkyl-S(═O)$_2$F;
- J is H, $OR^a$, $NR^bR^c$, or J and G taken together form an alkyl bridge;
- $R^1$ is H, —$(C_1\text{-}C_8)$alkyl, —$(C_1\text{-}C_8)$cycloalkyl, —C(═O)$R^d$, or —S(═O)$_2R^e$;
- $R^2$ is H, $OR^f$, —$(C_0\text{-}C_5)$C(═O)$R^f$, —$(C_0\text{-}C_5)$C(═O)O$R^f$, —$(C_0\text{-}C_5)$OC(═O)O$R^f$, wherein $R^f$ is —$(C_1\text{-}C_8)$alkyl wherein —$(C_1\text{-}C_8)$alkyl is substituted optionally with amine;
- $R^3$ is H, —$(C_1\text{-}C_8)$alkyl, or —$(C_1\text{-}C_8)$cycloalkyl;
- $R^4$ is H or $R^3$ and $R^4$ taken together form a single bond; and
- $R^5$ is H, halo, or —$(C_1\text{-}C_8)$alkyl;

wherein —$(C_1\text{-}C_8)$alkyl is unsaturated or saturated and unbranched or branched, —$(C_1\text{-}C_8)$cycloalkyl comprises an optional ring heteroatom, and at least of one of J, G, or $R^1$ comprises —S(═O)$_2$F. In various embodiments, G is $CHNR^b(C_1\text{-}C_8)$alkyl-$SO_2X$ wherein X is halo or F. In various embodiments, $R^b$ and/or $R^c$ is —$(C_1\text{-}C_8)$alkyl-$SO_2X$.

In some embodiments, the compound is TJ-171 (also known as TJ-4-171):

(TJ-171)

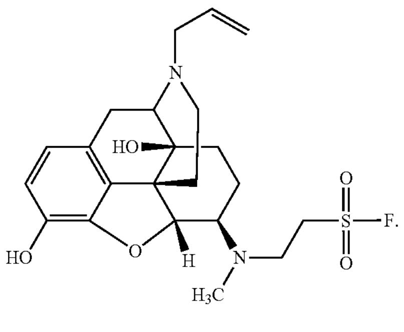

In some embodiments, the compound of Formula I is a compound of Formula II:

(II)

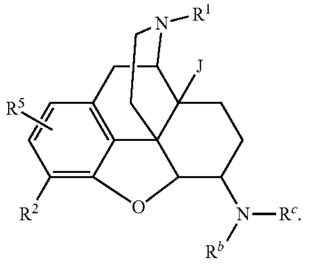

In some embodiments, the compound of Formula I is a compound of Formula III:

(III)

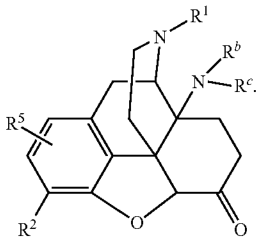

In some embodiments, the compound is TJ-345:

(TJ-345)

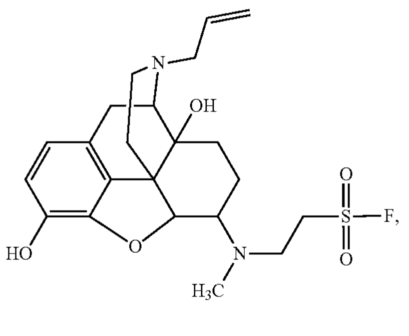

or a stereoisomer thereof.

This disclosure also provides a compound of Formula IIA:

(IIA)

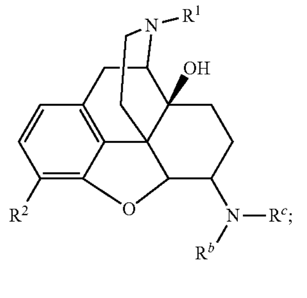

wherein $R^1$ is —($C_1$-$C_3$)alkyl-CZ═$CZ_2$ wherein Z is H, Me, or $CF_3$, —CH(Me)-CH═$CH_2$, —($C_1$-$C_3$)alkyl-cyclopropyl, —CH(Me)-cyclopropyl, propargyl, arylsulfonamide-substituted triazole, or —$CH_2$-cyclopropyl wherein the cyclopropyl is substituted with hydroxymethyl and $R^F$ wherein $R^F$ is H, Me, F, or $CF_3$;

$R^2$ is $OR^{10}$ wherein $R^{10}$ is H, —C(═O)$R^{11}$, —C(═O)$OR^{11}$, —$CH_2$O—C(═O)$R^{11}$, —CH(Me)-O—C(═O)$R^{11}$, —$CH_2$O—C(═O)$OR^{11}$, or —CH(Me)-O—C(═O)$OR^{11}$, and $R^{11}$ is unbranched or branched —($C_1$-$C_8$)alkyl, —$CH_2NH_2$, —$CH_2NMe_2$, or —$CH_2$—N-morpholinyl;

$R^b$ is H, Me, —$CH_2CF_3$, —OH, —($C_3$-$C_8$)cycloalkyl, or propargyl; and $R^c$ is —S(═O)$_2$F, —($C_1$-$C_8$)alkyl-S(═O)$_2$F wherein the alkyl is optionally further substituted with bromo or chloro, —CH═CH—S(═O)$_2$F, phenyl substituted with —S(═O)$_2$F, tetrahydropyran substituted with —S(═O)$_2$F, or —($C_3$-$C_8$)cycloalkyl substituted with —S(═O)$_2$F and optionally further substituted by two fluorine atoms on a ring carbon;

or $R^b$ and $R^c$ taken together are —$CH_2$—$CH_2$—$SO_2$—.

In various embodiments, $R^1$ is allyl or —$CH_2$-cyclopropyl, and $R^2$ is OH.

This disclosure also provides a compound of Formula IIB:

(IIB)

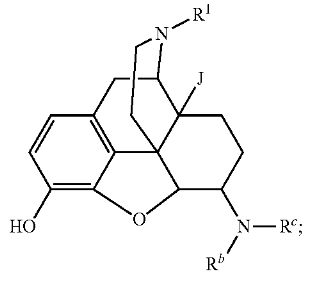

wherein $R^1$ is allyl or —$CH_2$-cyclopropyl;

J is OH or OMe;

$R^b$ is Me, —$CH_2CF_3$, —OH, —($C_3$-$C_8$)cycloalkyl, or propargyl; and $R^c$ is —S(═O)$_2$F, —($C_1$-$C_8$)alkyl-S(═O)$_2$F wherein the alkyl is optionally further substituted with bromo or chloro, —CH═CH—S(═O)$_2$F, phenyl substituted with —S(═O)$_2$F, tetrahydropyran substituted with —S(═O)$_2$F, or —($C_3$-$C_8$)cycloalkyl substituted with —$S(=O)_2F$ and optionally further substituted by two fluorine atoms on a ring carbon;
or $R^b$ and $R^c$ taken together are —$CH_2$—$CH_2$—$SO_2$—.
In various embodiments, the compound is:
1a (TJ-345)
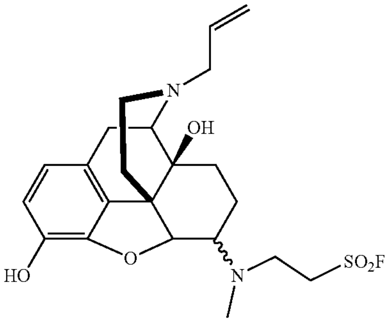
1b (TJ-3-343)
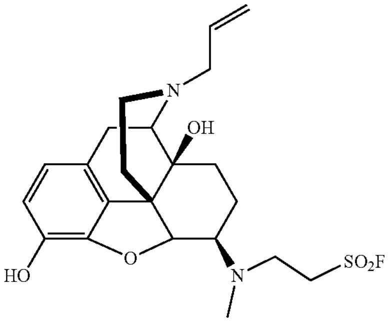
1c (TJ-4-485)
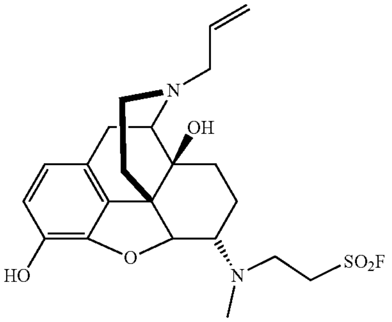
1d
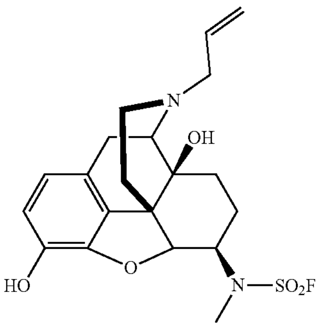
-continued
1e
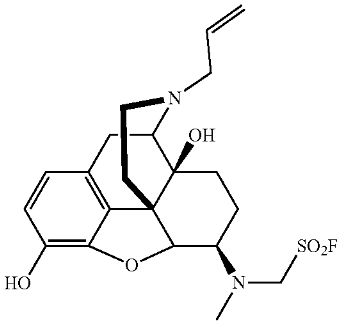
1f
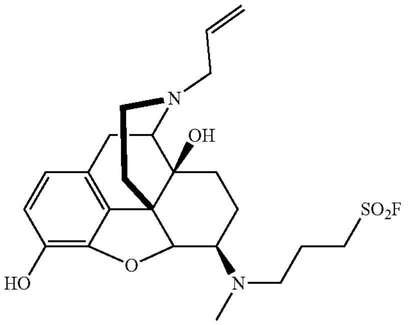
1g
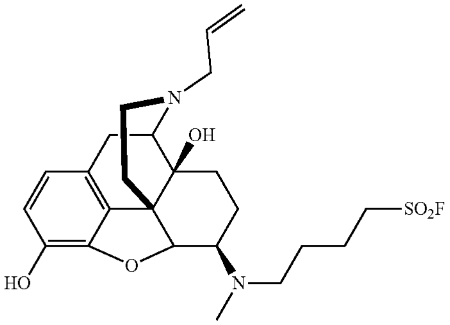
1h
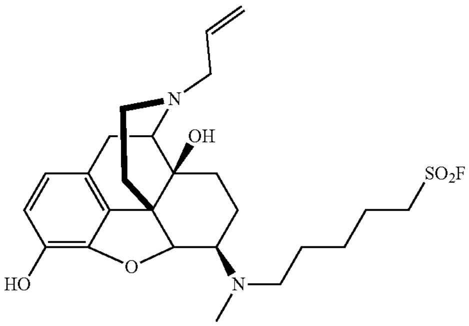

-continued
1i
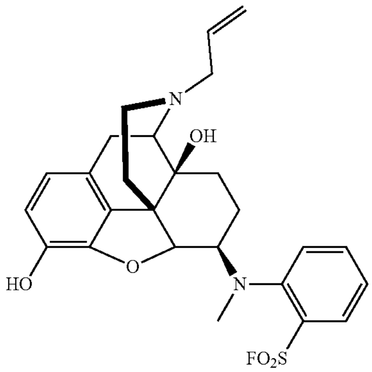
1j
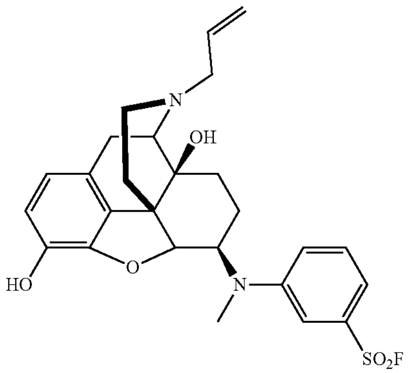
1k
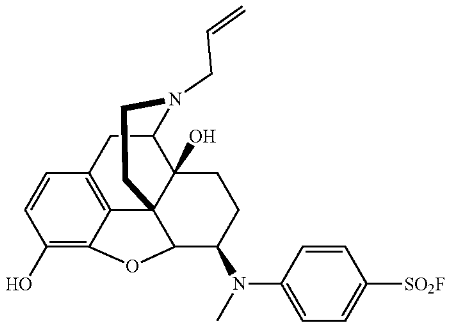
1l
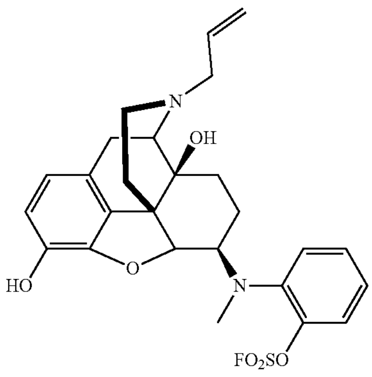
-continued
1m
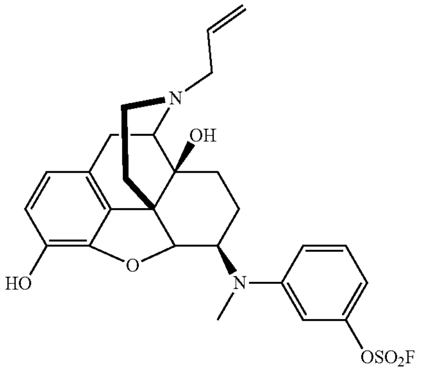
1n
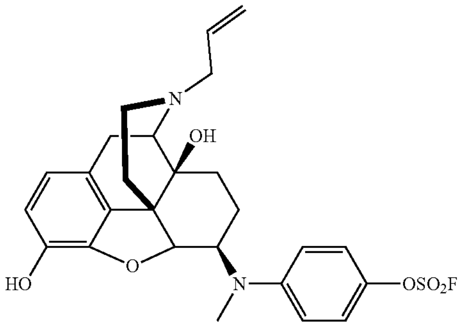
1n2
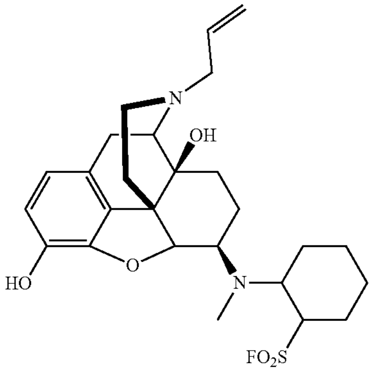
1o
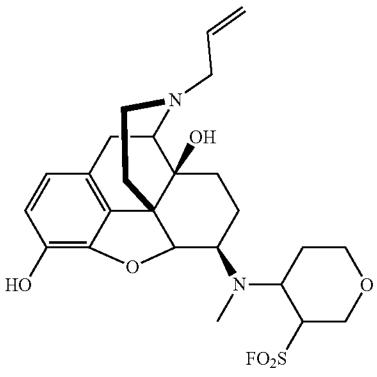

-continued
1p
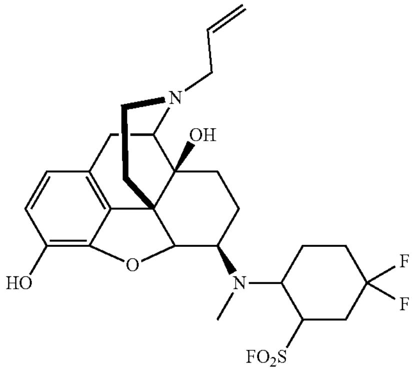
1q
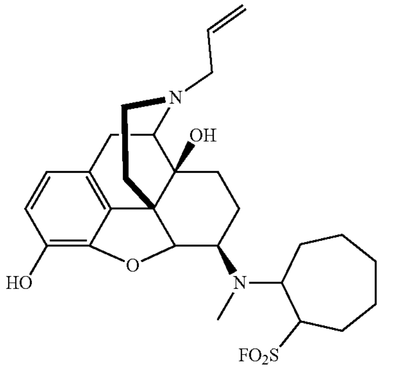
1r
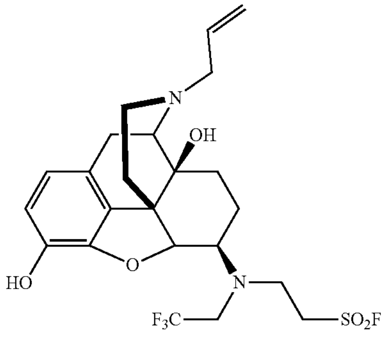
1s
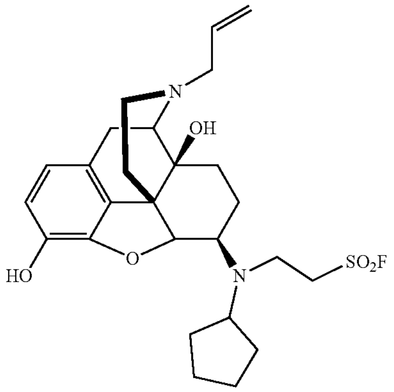
-continued
1t
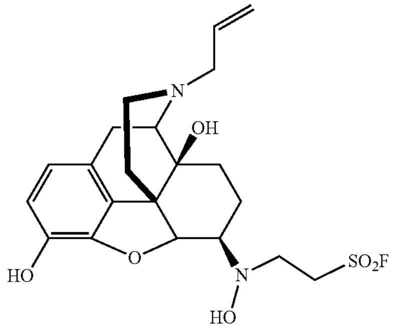
1u
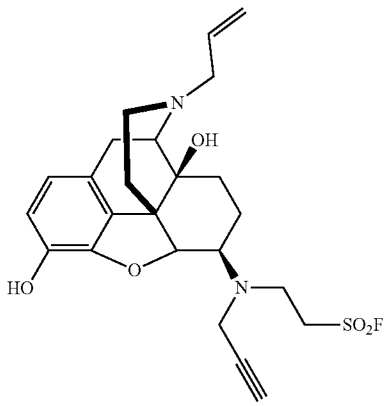
1v
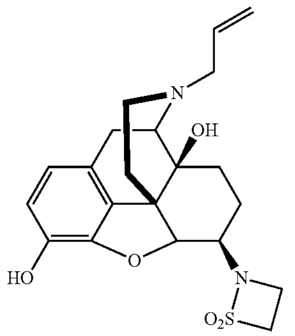
1w
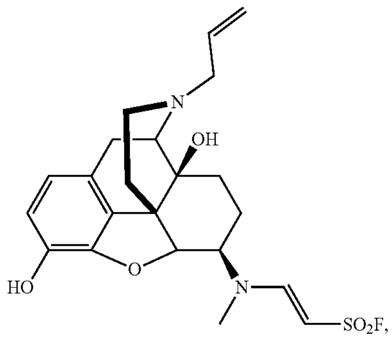
or -continued 1x

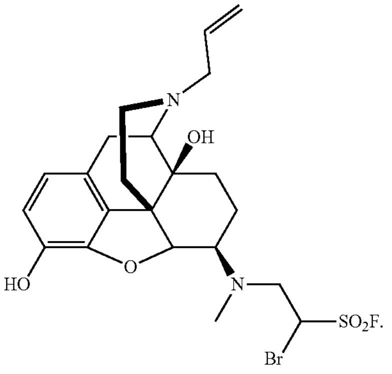

Additionally, this disclosure provides a compound of Formula IIC:

(IIC)

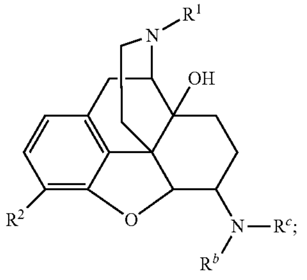

wherein $R^1$—($C_1$-$C_3$)alkyl-CZ═$CZ_2$ wherein Z is H, Me, or $CF_3$, —CH(Me)-CH═$CH_2$, —($C_1$-$C_3$)alkyl-cyclopropyl, —CH(Me)-cyclopropyl, propargyl, arylsulfonamide-substituted triazole, —$CH_2$-cyclopropyl wherein the cyclopropyl is substituted with hydroxymethyl and $R^F$ wherein $R^F$ is H, Me, F, or $CF_3$, —($C_1$-$C_8$)alkyl-S(═O)$_2$F, phenyl substituted with —S(═O)$_2$F, phenyl substituted with —OS(═O)$_2$F, —CH═CH-Ph substituted with —S(═O)$_2$F, —CH═CH-Ph substituted with —OS(═O)$_2$F, or phenyl substituted with —CH═CH—S(═O)$_2$F;

$R^2$ is $OR^{10}$ wherein $R^{10}$ is H, —C(═O)$R^{11}$, —C(═O)$OR^{11}$, —$CH_2$O—C(═O)$R^{11}$, —CH(Me)-O—C(═O)$R^{11}$, —$CH_2$O—C(═O)$OR^{11}$, or —CH(Me)-O—C(═O)$OR^{11}$, and $R^{11}$ is unbranched or branched —($C_1$-$C_8$)alkyl, —$CH_2NH_2$, —$CH_2NMe_2$, or —$CH_2$—N-morpholinyl;

$R^b$ is Me; and $R^c$ is —($C_1$-$C_8$)alkyl-S(═O)$_2$F.

In various embodiments, $R^1$ is allyl or —$CH_2$-cyclopropyl, and $R^2$ is OH.

This disclosure provides a compound of Formula IIIA:

(IIIA)

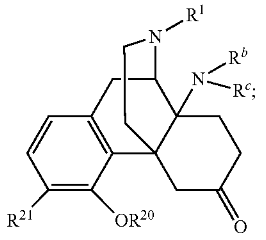

wherein $R^1$ is allyl or —$CH_2$-cyclopropyl;

$R^b$ is H;

$R^c$ is —C(═O)—$R^{12}$ or —S(═O)$_2$—$R^{13}$.

$R^{12}$ is —($C_1$-$C_3$)alkyl-CZ═$CZ_2$ wherein Z is H, Me, or $CF_3$, —CH(Me)-CH═$CH_2$, —($C_1$-$C_3$)alkyl-cyclopropyl, —CH(Me)-cyclopropyl, propargyl, arylsulfonamide-substituted triazole, —$CH_2$-cyclopropyl wherein the cyclopropyl is substituted with hydroxymethyl and $R^F$ wherein $R^F$ is H, Me, F, or $CF_3$, —($C_1$-$C_8$)alkyl-S(═O)$_2$F, phenyl substituted with —S(═O)$_2$F, phenyl substituted with —OS(═O)$_2$F, —CH═CH-Ph substituted with —S(═O)$_2$F, —CH═CH-Ph substituted with —OS(═O)$_2$F, or phenyl substituted with —CH═CH—S(═O)$_2$F;

$R^{13}$ is —($C_1$-$C_8$)alkyl-S(═O)$_2$F, phenyl substituted with —S(═O)$_2$F, phenyl substituted with —OS(═O)$_2$F, —CH═CH-Ph substituted with —S(═O)$_2$F, —CH═CH-Ph substituted with —OS(═O)$_2$F, or phenyl substituted with —CH═CH—S(═O)$_2$F;

$R^{20}$ is H or —($C_1$-$C_8$)alkyl; and $R^{21}$ is H or —C(═O)$NH_2$.

The disclosure also provides a method to treat a drug overdose, for example, an opioid overdose, comprising administering an effective amount of a mu-opioid antagonist of a formula described herein to a subject in need thereof, wherein the antagonist covalently binds to mu-opioid receptors of the subject via the sulfur(VI) fluoride group when the antagonist is in contact with the mu-opioid receptors, thereby treating the drug overdose. In some embodiments, the binding is selective for the mu-opioid receptor over other receptors, such as the kappa or delta opioid receptors. In other embodiments, the binding of a compound described herein is selective for the kappa opioid receptor, or for the delta opioid receptor.

In some embodiments, the antagonist has a pharmacological duration of action in the subject at least twice the time of a corresponding a mu-opioid antagonist that does not comprise a sulfur(VI) fluoride group. In some embodiments of the method, the antagonist is TJ-345:

(TJ-345)

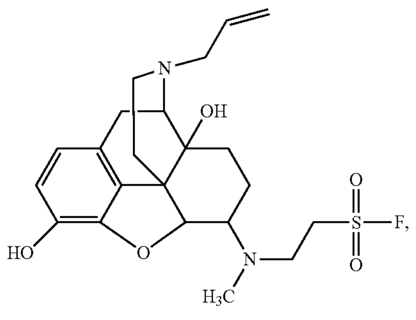

or a stereoisomer thereof, for example TJ-171.

Discussion

The recently discovered SuFEx technology, and specifically the use of $SO_2$—F warhead in a highly selective biocompatible reaction for proximity-guided covalent attachment in vivo, has never been applied to solving the problem of opioid overdoses. Combining the proximity-guided click chemistry moiety with a selective morphinan scaffold to achieve high antagonist efficacy at the MOR and low cellular toxicity is also a new approach to the problem. 3D modeling of the covalent ligand binding stages was used to satisfy the critical requirement of ligand binding to MOR and correct positioning of the reactive warhead at a Tyr residue in the pocket. The compound TJ-345 has been demonstrated to be a lead compound that can be readily derivatized to provide other potent antagonists. Various lead compounds are currently being evaluated for ADME/PK properties and eventually toxicology profiling, thus allowing for clinical development.

Robust and prolonged reversal of fentanyl overdose requires long-acting antagonists that irreversibly bind to MOR and block fentanyl action. Assessment of TJ-345 shows that the proximity-guided SuFEx chemistry can be used to rationally design antagonists that bind selectively to MOR orthosteric pocket and covalently attach to a Tyr side chain in the pocket. Improved antagonist potency, faster binding kinetics of inhibition, and increased selectivity to MOR vs. other opioid receptor subtypes can be achieved by selectively altering the substituents of the compounds described herein.

Design. Selective SuFEx antagonists to MOR were rationally designed using structure-based modeling to functionalize naloxone scaffold with $SO_2$—F warheads (Scheme 1 below). Our model based on the MOR crystal structure with antagonist β-FNA indicated that the carbonyl group of naloxone is a suitable point for derivatization as it is chemically accessible and is not involved in interactions with the receptor. There are three accessible Tyr residues in the MOR pocket, Tyr77, Tyr130, and Tyr150. Of them, Tyr150 in proximity to the carbonyl of the docked naloxone was selected as an initial target. Candidate ligands for covalently attaching to Tyr150 have been assessed computationally by modeling their initial non-covalent binding pose, transition state, and the final chemically attached compound. About 12 derivatives with the best binding scores were synthesized and tested, two of which showed remarkably high in vitro potency.

Chemical synthesis. Compounds 2, 3, 4, TJ-345, and others were synthesized via reductive amination of naloxone followed by the conjugate addition of ethenesulfonyl fluoride, as shown in Scheme 1 (initial synthetic steps performed according to a modified version of previously reported procedure (Ref. 1: Mohamed et al., *J. Med. Chem.* 1986, 29(8), 1551-1553)). In the case of TJ-345, equal amounts of 6α and 6β epimeric methylamino intermediates were formed using the method of Mohamed at al. A method was then developed to separate its isomer TJ-343 (6-α ethyl), and more recently the isomer TJ-4-171 (6-β ethyl). Compounds were purified to >95% purity by HPLC and their structures were confirmed by high-resolution MS, $^1H$ NMR and $^{13}C$ NMR spectroscopy.

Scheme 1. Design of $SO_2F$-containing covalent ligands targeting Y150 of human MOR: synthesis of covalent ligands with alkyl axial/equatorial substitutions in the 6th position.

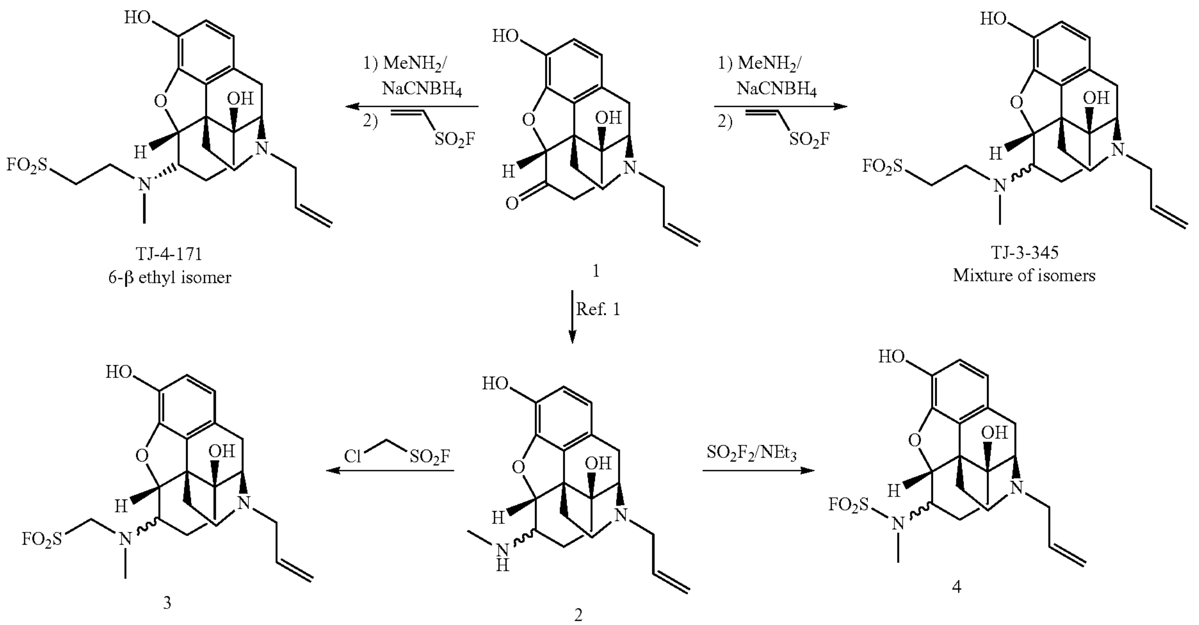

TJ-4-171
6-β ethyl isomer

1

TJ-3-345
Mixture of isomers

3

2

4

HRMS (ESI—TOF, acetonitrile/water 1:10 to 10:1 gradient, 0.05% v/v formic acid, M + H): compound 3: calculated: 439.5224, found 439.5231; compound 4: calculated: 425.1546, found 425.1538.

Figure 2:
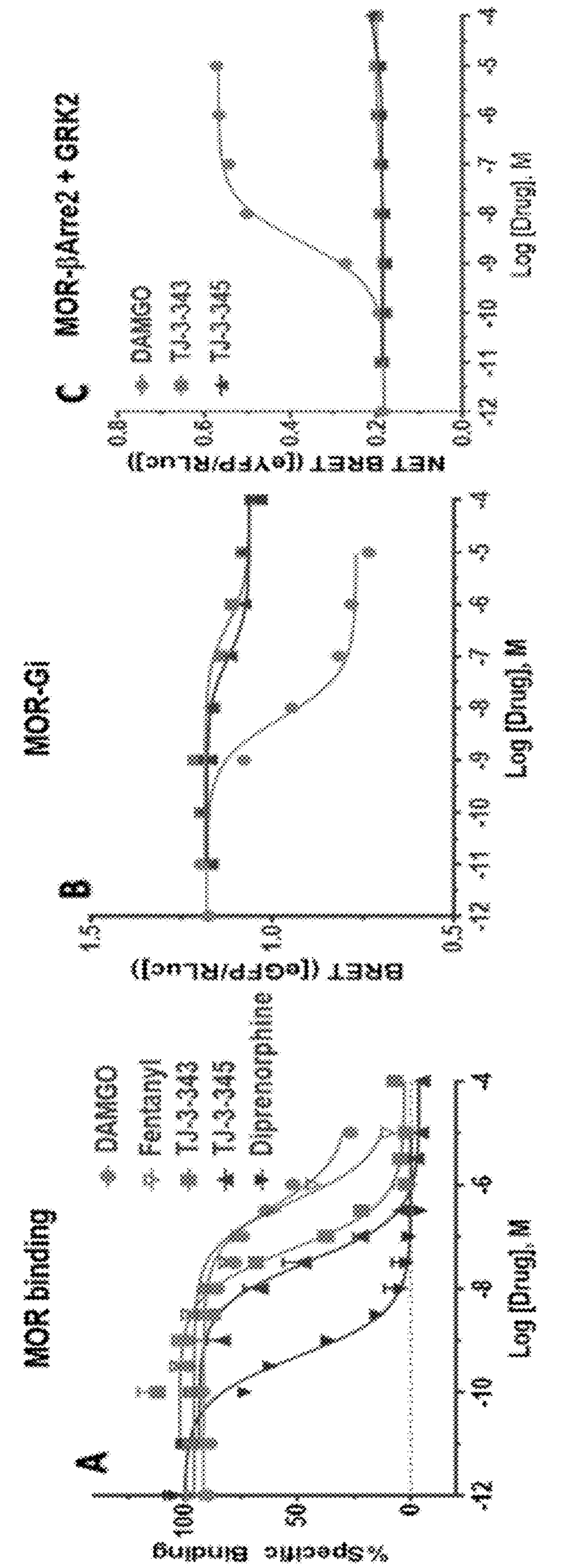
FIG. 2. In vitro characterization of TJ-343/TJ-345. (A) Radioligand binding, (B) G-protein recruitment, and (C) Arrestin recruitment.
Figure 3:
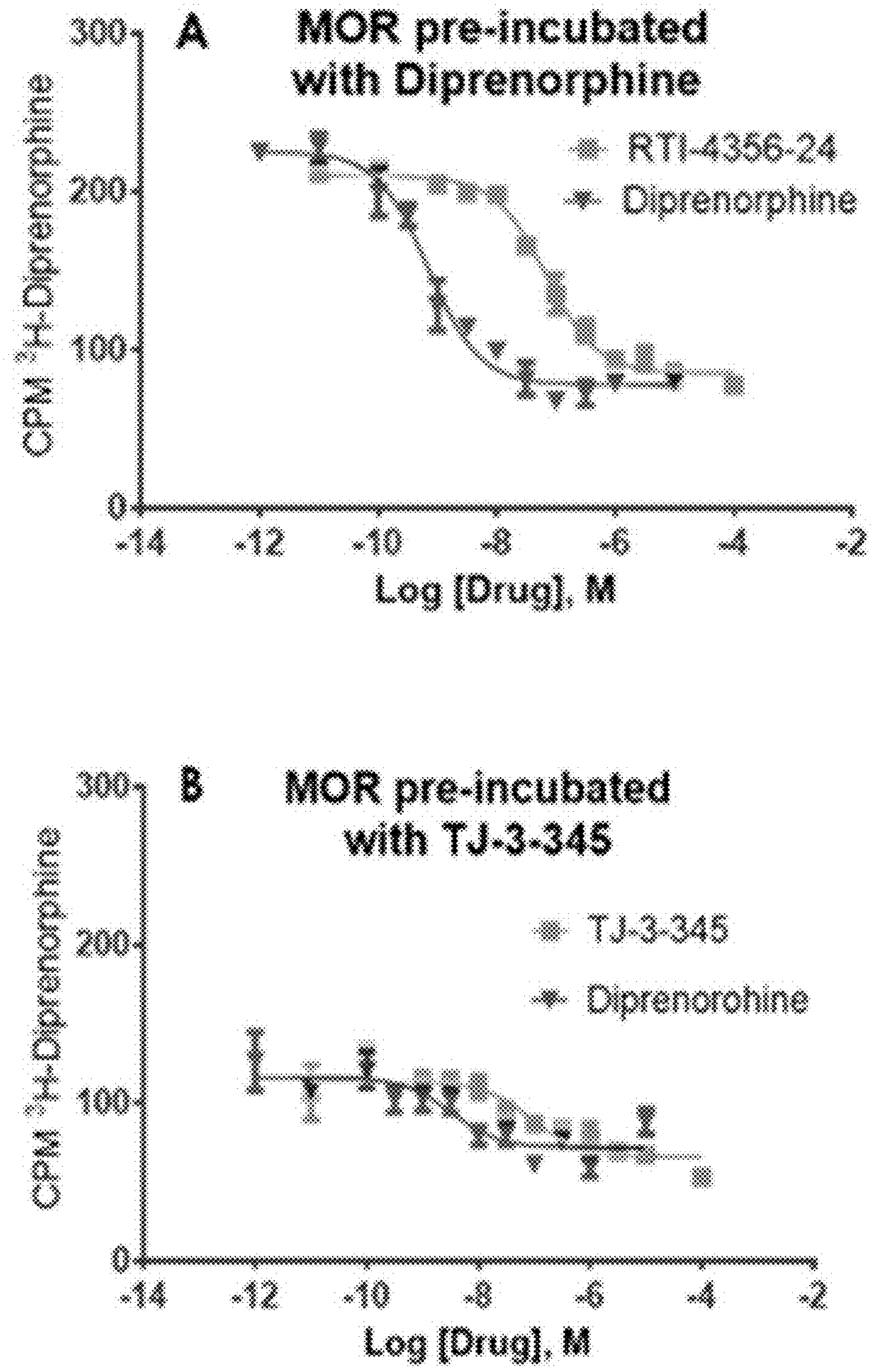
FIG. 3. Irreversible attachment of TJ-345 (B), but not Diprenorphine or RTI-4356-24 (A) effectively blocks binding of other ligands after TJ-345 was washed away 5 times.

In Vitro Characterization of TJ-345 as an irreversible antagonist of MOR. In vitro assays characterized irreversible binding and antagonist potency of the TJ-343/345 compounds. TJ-345 shows better high-affinity binding to MOR than fentanyl and DAMGO (a synthetic opioid peptide) ($K_i$=15 nM compared to $K_i$=149 nM and 125 nM, respectively) in radioligand competition assays (FIG. 2A). The affinity of TJ-345 is thus comparable to carfentanyl ($K_i$=6.6 nM, not shown), indicating it can be effective in counteracting super-potent opioids. In functional assays, TJ-345 showed only traces of partial agonism (<10% $E_{max}$) as measured by G protein recruitment (FIG. 2B), without any detectable arrestin recruitment activity (FIG. 2C). Finally, TJ-345 was shown to be an irreversible antagonist at MOR as it maintained a nearly full blockade of radioligand $^3$H-Diprenorphine binding for >48 hours after TJ-345 was washed away 5 times (FIG. 3).

The SuFEx antagonists target the Tyr150 side chain for $SO_2$—F attack, yielding the first long-acting irreversible lead TJ-345 ($K_i$=15 nM). Current SAR is being used to identify more potent and selective leads. The alkyl-$SO_2$—F warhead is flexible and works for short alkyl linkers (n=1-4). The aryl-O—$SO_2$—F moiety should allow for contact to the more distant Tyr side chains in the pocket, while maintaining its selectivity on a whole proteome level due to higher rigidity.

The preparation of cyprodime analogs with the aryl-O—$SO_2$—F warhead and other antagonists are shown below in Scheme 2; see also, Example 2 (further below). For example, compound 6 can be synthesized by converting cyprodime (5) or samidorphan to a hydroxy analog followed by azidation and Staudinger reaction (where the warhead attachment point is different from naloxone). Compounds 7a-f and 8a-f can be obtained by coupling 6 with corresponding acyl chloride and sulfonyl chloride, respectively. The fluorosulfate 9 can be synthesized by demethylation of cyprodime and subsequent treatment with $SO_2F_2$ gas under basic conditions.

Scheme 2. Preparation of aryl-O—$SO_2$—F and aryl-$SO_2$—F containing covalent ligand targeting residues $Y_{150}$ and $Y_{130}$ with MOR-selective cyprodime scaffold: synthesis of second-generation covalent ligands with aryl-O —$SO_2$—F and aryl-$SO_2$—F warheads (Ref A: McLaughlin et al., *J Biol Chem.* 2004 Jan 16; 279(3): 1810-1818).

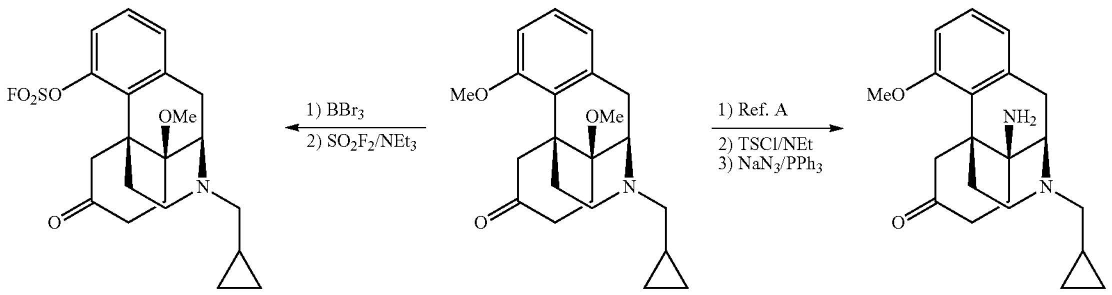

9 5 6

6 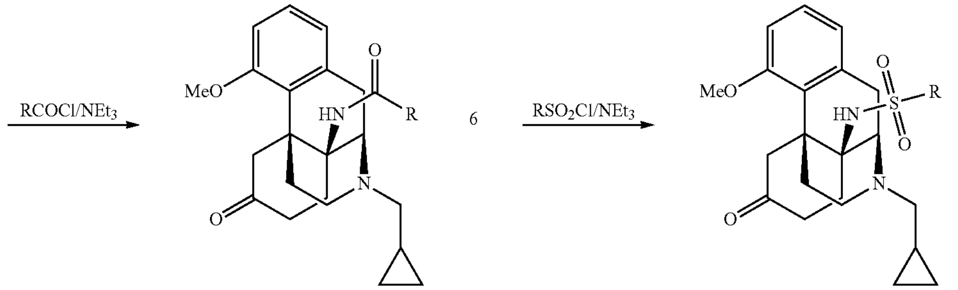

7 6 8

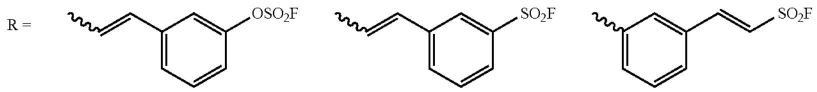

7a-8a 7b-8b 7c-8c

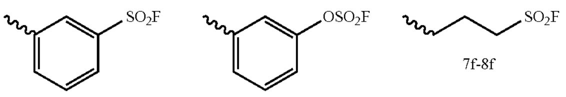

7d-8d 7e-8e 7f-8f

Modification of the morphinan scaffold to enhance potency, selectivity and ADME/PK properties of the compounds are underway. Based on the prior metabolism studies of naloxone, the phenol and the allylamine moieties may be metabolically labile. Several modifications of N-substituents can both optimize potency for MOR as well as block the CYP mediated oxidations of the allylamine fragment. The introduction of a methyl substituent at the $CH_2$ group i.e. (—N—$CH(CH_3)$-allyl) is one example. The strategy has been used previously in the opioid field to design PPL101 and PPL103 (Khroyan et al., *Frontiers in Psychiatry* 8, 52, (2017)). Several additional N-substituents may also enhance affinity and potency for opioid receptors. Similarly, prodrugs to block first-pass metabolism of the phenol group to sulfate or glucuronide are under evaluation. Esters, carbonate, and a soft alkyl approach can fine-tune the hydrolysis rate. To increase solubility, amines can be included in the prodrug pro-moiety as well. On the cyprodime scaffold, we anticipate the N-CPM group to be labile and thus can be substituted using strategies similar to those of the naloxone template (see Scheme 3). The methoxy group may also be labile. A sterically hindered ether may be used in place of the methoxy to reduce lability. Similar strategies can be pursued on a samidorphan template.

Scheme 3. Preparation of compounds designed to block metabolism of phenol and/or optimize potency and metabolism of N-$CH_2$-allyl groups.

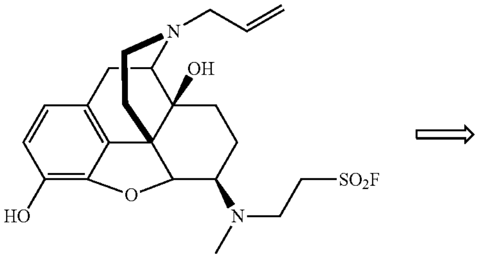

TJ-345
racemic or specific isomers

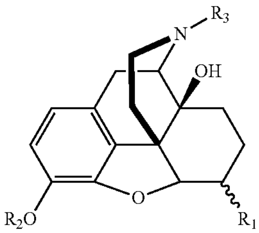

$R_1$ = Optimized substituents
(e.g., —$N(R_a)(R^b)$)

-continued

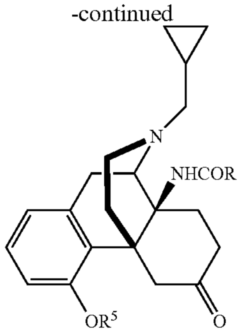

Cyprodime analogue
($R = R_1, R_2,$ or $R_3$)
$R_2$ = metabolicly labile groups

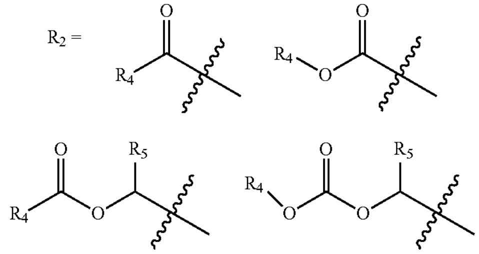

$R_4$ = —$CH_3$, —$C_2H_5$, t-butyl, —$CH_2$—$N(CH_3)_2$

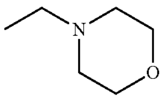

$R_5$ = H or $CH_3$

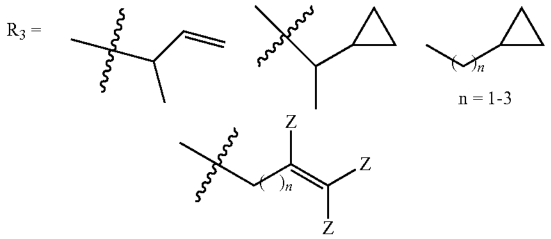

Z = H, $CH_3$, F or $CF_3$
n = 1-3

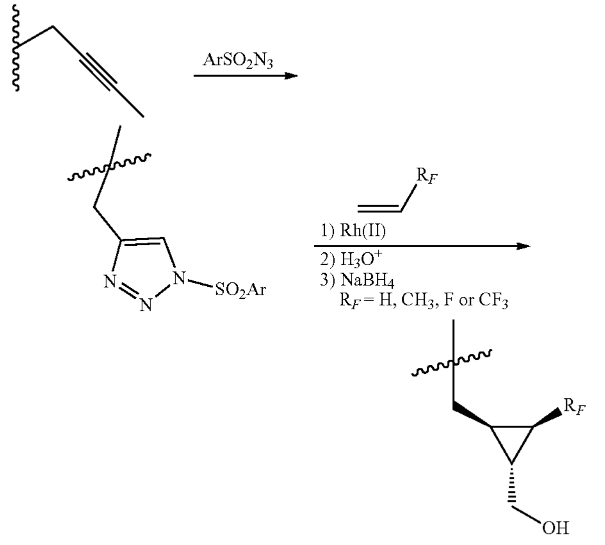

Evaluation of in vitro ADME/PK. The metabolism of compounds can be studied in mouse and human liver microsomes and plasma using LC-MS/MS. Test compounds at 1 μM can be incubated with 1 mg/mL mouse and human microsomes and NADPH at 37° C. with continuous shaking to determine the rate of metabolism. Samples can be collected at 0, 5, 10, 30, 60, and 120 min and the concentration of test compounds determined using LC-MS/MS. For compounds with metabolic liability, metID studies can be used to identify metabolic soft spots on molecules. A plasma and microsomal stability of >2 hours is preferred. For prodrugs, this assay can be used to ensure complete hydrolysis to the active compound.

Brain permeability proxy assays. The in vitro MDR1-MDCK assay can be used as a model for detection of P-gp substrates and inhibitors and to predict brain uptake potential. P-gp is one of the most well-recognized efflux transporters in the brain, kidney and intestine. Cell monolayers can be used to assess bidirectional permeability, efflux ratio, and compound recovery. Screening results can be used as a proxy for brain/plasma exposures.

Results for TJ-345 show that SuFEx covalent ligands can be designed to inhibit MOR activity in vitro, as well as in vivo in mice for an extended period of time. Pretreatment with the antagonist compounds can be used to validate protection against fentanyl-induced respiratory depression, while administration after fentanyl exposure evaluates the capacity of the antagonists to reverse and rescue subjects from a lethal fentanyl overdose, defining a therapeutic window whereupon an overdose can be reversed but not precipitate opiate withdrawal.

Figure 4:
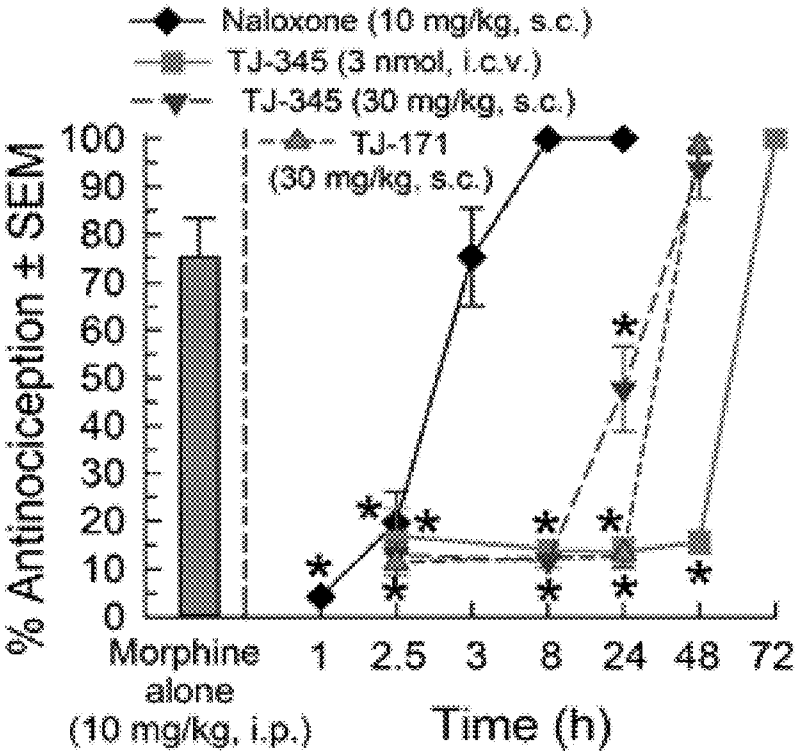
FIG. 4. (A) Duration of naloxone (♦) and TJ-345 (■,▼) antagonism of the MOR agonist morphine in the 55° C. WWTW assay. Points=8-10 mice, tested once. *$p<0.05$ vs morphine; Dunnett's test. TJ-345 (■): ($F_{(5,49)}=42.6$, $p<0.0001$); TJ-345 (▼): ($F_{(4,41)}=23.6$, $p<0.0001$); Naloxone (♦): ($F_{(5,56)}=31.5$, $p<0.0001$); TJ-171 (▲): ($F_{(3,40)}=60.1$, $p<0.0001$) each by 1-way ANOVA. (B) Antagonism of the MOR agonist morphine by TJ-345 administered through subcutaneous (s.c.) route. N=8-10 mice/point. *$p<0.05$) vs morphine alone.
Figure 4:
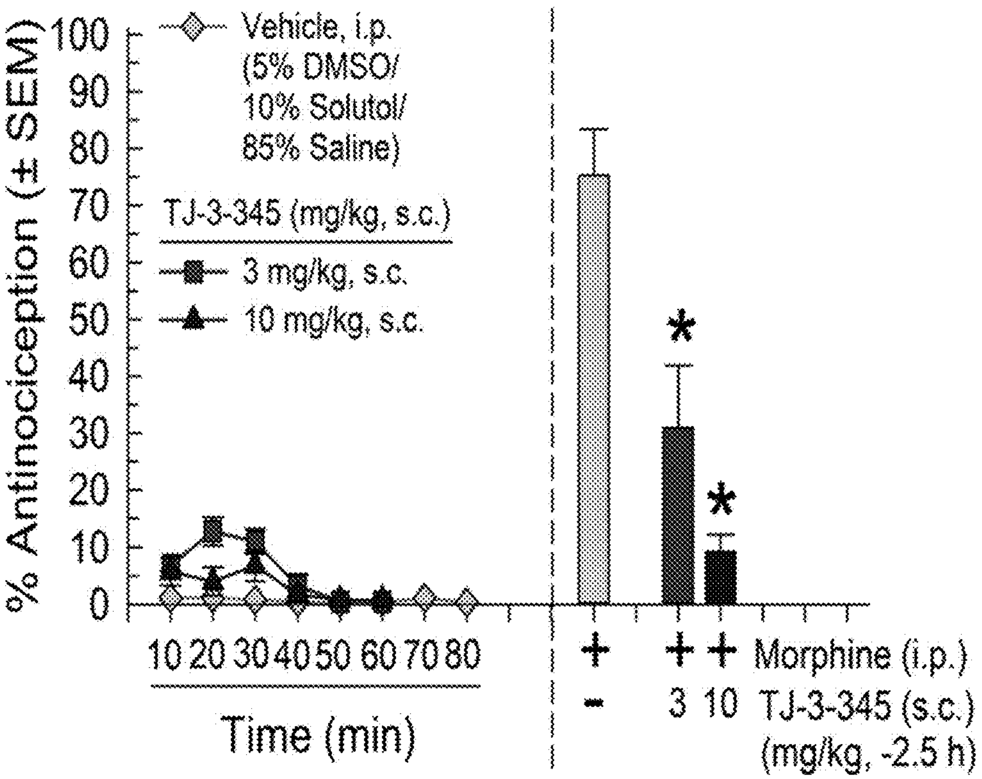

In vivo characterization of TJ-345 and TJ-171 in i.c.v. and s.c. delivery (FIGS. 4-7). Compounds were characterized for their antagonist properties using the mouse 55° C. warm-water tail withdrawal (WWTW) assay (FIG. 4). TJ-345 dose-dependently antagonized morphine antinociception after i.c.v. (3-300 nmol, but not 0.3 nmol; $F_{(5,48)}=8.42$, $p<0.0001$) or s.c. pretreatment (3-60 mg/kg, but not 1 mg/kg; $F_{(5,48)}=33.3$, $p<0.0001$); 1-way ANOVA w/Tukey tests. TJ-345 significantly antagonized morphine up to 48 hours after a 3 nmol i.c.v. but showed only partial blockade of morphine at 24 h after a 30 mg/kg s.c. treatment.

In contrast, TJ-171 fully antagonized morphine at 24 h after a 30 mg/kg s.c. treatment (▲, FIG. 4). This compared favorably to naloxone (♦, 10 mg/kg, s.c.), which was only effective for the first 2.5 hours after treatment. The duration of TJ-171 antagonism was consistent with the reported turnover time of the MOR in mice. Higher doses of TJ-345 (>30 nmol i.c.v. or 60 mg/kg, s.c.) displayed weak (~15%) transient antinociception in the first 40 min after treatment (data not shown), which could exacerbate fentanyl effects. In contrast, the TJ-171 did not display antinociception, indicating improved antagonism by using TJ-171.

Figure 5:
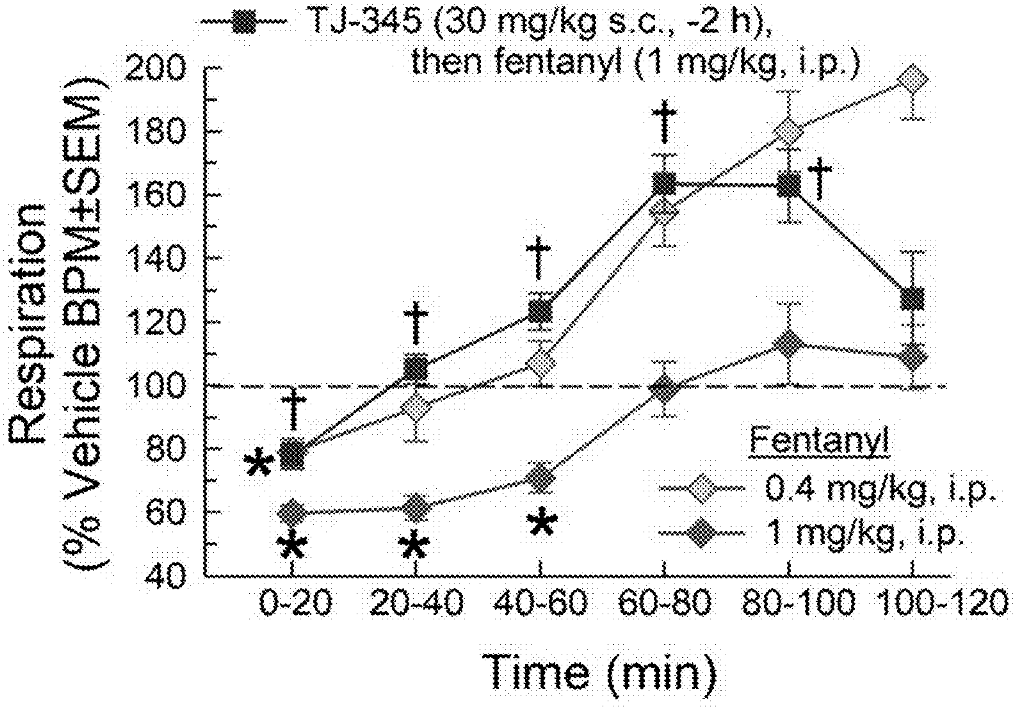
FIG. 5. Dose- and time-dependent A) respiratory depression and B) spontaneous locomotor effects of fentanyl alone (diamonds) or after a 2 h pretreatment with TJ-345 (30 mg/kg, s.c., ■) evaluated in the CLAMS with C57BL/6J mice. *$p<0.05$ vs vehicle effect (dashed line); †$p<0.05$ vs fentanyl (1 mg/kg); 2-way RM ANOVA with Tukey's post hoc test. N=12 mice/set. Dashed line=normalized saline response (N=20 mice).
Figure 5:
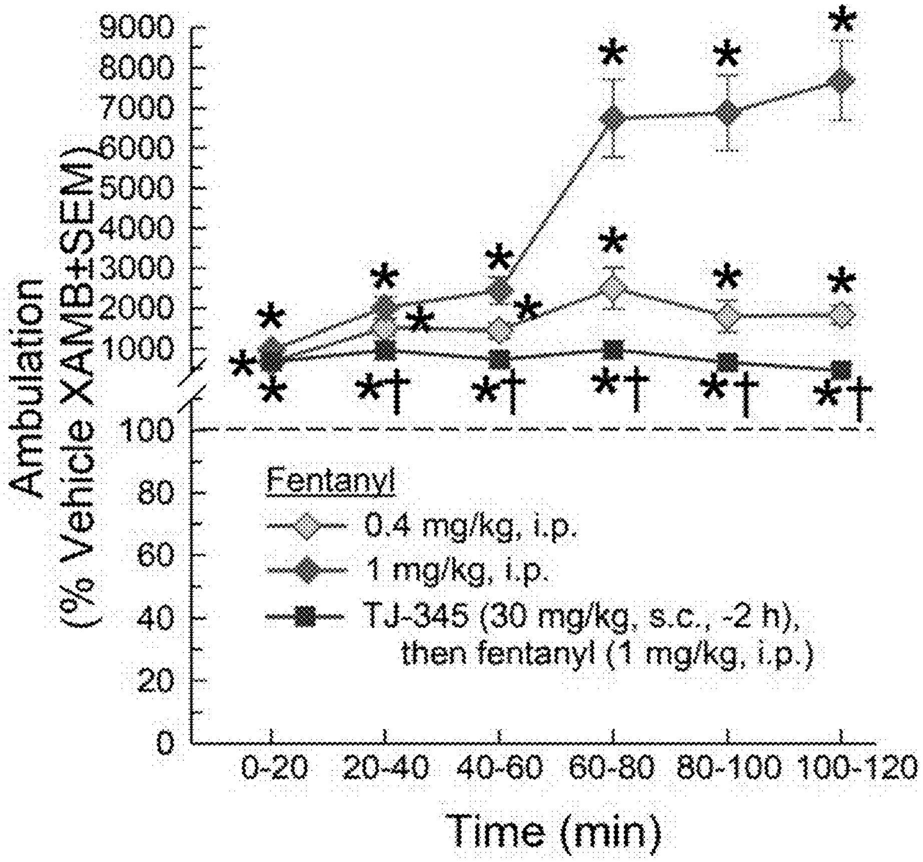
Figure 6:
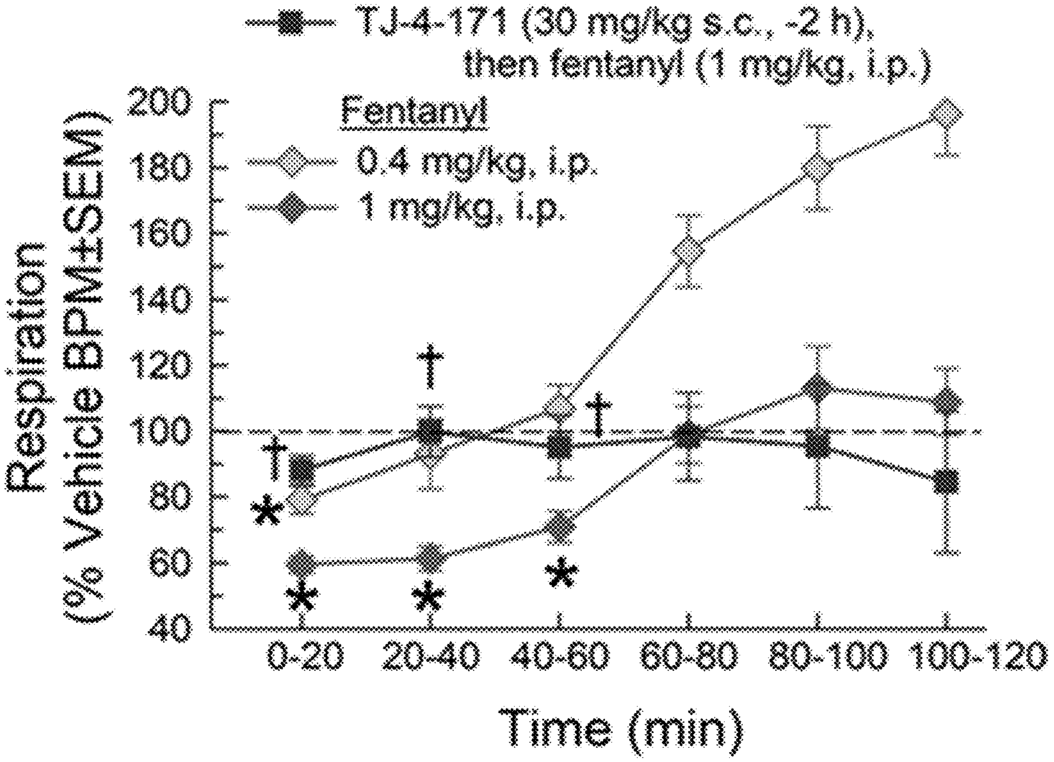
FIG. 6. Same experiment as in FIG. 5, but for compound TJ-4-171.
Figure 6:
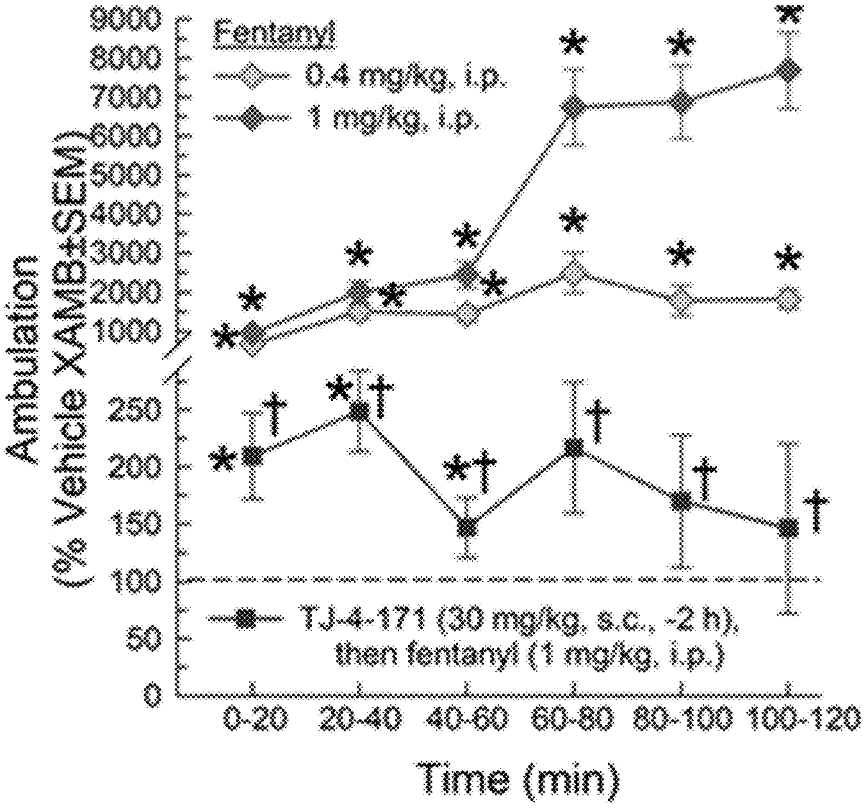

As expected of a MOR agonist, fentanyl induced significant time- and dose-dependent respiratory depression ($F_{(10,185)}=11.3$, $p<0.0001$) and hyper-ambulation ($F_{(10,185)}=51.16$, $p<0.0001$; 2-way RM ANOVA) in mice measured in the Comprehensive Lab Animal Monitoring System (CLAMS; FIG. 5). A 2 hour pretreatment with TJ-3-345 (30 mg/kg, s.c.) significantly reversed fentanyl-induced respiratory depression ($F_{(15,240)}=10.3$, $p<0.0001$) and hyperlocomotion ($F_{(15,240)}=45.6$, $p<0.0001$) (FIG. 5). Similar assays for its 6-β ethyl isomer TJ-4-141 (FIG. 6) indicate that the blockade of fentanyl is mostly mediated by this isomer of TJ-345, supporting that stereospecificity is important for the intended activity. Importantly, efficacy of the TJ-345 and TJ-4-171 after s.c. administration indicate their acceptable blood-brain barrier permeability.

The major objective of the administration of the compounds described herein is an acute reversal agent for fatal opiate overdose (see Table 1). A therapeutic window that reverses coma and respiratory depression but causes minimal to mild precipitated withdrawal symptoms is under development. Even if only a Minimum Acceptable Product Profile (MAPP) is achieved and the drug is used only in known fentanyl or fentanyl-related overdoses as a second-line treatment for cases refractory to naloxone, it would represent a transformative new therapy that would save the lives of those threatened by opiate overdose. The covalent MOR antagonists can also be used as a prophylaxis agent against threatened exposure with highly potent opioids like fentanyl and its synthetic derivatives.

TABLE 1

Target Product Profile

| Product Properties | Minimum Acceptable Product Profile (MAPP) | Target Product Profile (TPP) |
|---|---|---|
| Primary Indication | Opioid overdose with suspicion of fentanyl or a fentanyl derivative | All opioid overdose cases |
| Patient Population | Adults with life-threatening opioid overdose who are refractory to naloxone | Adults and children with opioid overdose |
| Route of Administration | Single dose; Intramuscular; Pre-filled syringe | Single dose; Intramuscular; Autoinjector |
| Regimen | Administer after the patient has had a partial but not full response to naloxone | Administer directly after signs of opioid overdose |
| Efficacy | Reversal of respiratory depression | Reversal of respiratory depression |
| Risks/Side effects | Moderate opioid withdrawal symptoms<br>Minor GI side effects<br>No cardiovascular/respiratory effects | Minimal opioid withdrawal symptoms<br>No GI side effects<br>No cardiovascular/respiratory effects |

Therapeutic Compounds.

The antagonist compound structures are based on the premise that preferential binding of the "chassis" (e.g. naloxone) to a specific receptor can be combined with a proximity-guided "warhead" (e.g. $SO_2F$), so that the initial and reversible receptor binding of the chassis is further enforced by the covalent attachment of the warhead to a specific residue of the receptor. Exquisite selectivity is thereby achieved from two independent events: reversible binding and "stapling" of the ligand in place once a covalent bond is formed. The platform allows for modular ligand design and preparation of additional compounds of the invention using structure-based modeling of ligand interactions in the binding pocket, where both the selective ligand chassis and the warhead can be varied. Specifically, the warhead connection to the chassis via linker can be designed to assure that the initial binding of the chassis into the pocket optimally positions the warhead for effective reaction with the selected receptor sidechain.

Unlike the other well-studied electrophilic warheads used for protein modification (such as fluorophosphonates, vinyl sulfones, and acrylamides), compounds of various formulas described herein contain sulfur(VI)-fluoride functional groups, —$SO_2F$ and —O—$SO_2F$. Their electrophilic sulfur atom can react with a nucleophile, such as the phenol group of tyrosine (Tyr) side chain, in a reaction called SuFEx. (FIG. 1). In contrast to previous warheads, these sulfur(VI) functional groups are exceedingly weak electrophiles that require tight protein binding and accurate reactant positioning for the reaction to occur. In our case, a selective ligand chassis, MOR ligand naloxone, functionalized with a SuFEx warhead, is capable of positioning the warhead precisely at a selected Tyr side chain in MOR binding pocket and ensure covalent reaction exclusively with MOR.

The risk of cellular toxicity and off-target effects is very low because such bond-forming events take place only when the selection step, i.e., binding to the receptor, is sufficiently driven by selective ligand-receptor interactions. An exceptionally high receptor-selectivity has been demonstrated in a cell-based study where SuFEx functionalized ligands selectively bound to the targeted intracellular lipid-binding protein (iLBP) family without any substantial interference with the other cell components. This and other emerging studies drive applications of SuFEx platform in drug discovery, including treatments of cancer, bacterial infections, and other conditions.

Our model based on the MOR crystal structure with antagonist β-FNA suggested that the carbonyl group of naloxone is a suitable point for derivatization as it is chemically accessible and is not involved in interactions with the receptor. Out of three accessible Tyr residues in the MOR pocket, Tyr150 is positioned in proximity to the carbonyl of the docked naloxone, and thus was selected as a target for drug design. Compounds TJ-343 (6-α ethyl isomer) and TJ-345 (α/β racemate) were synthesized via reductive amination of naloxone followed by the conjugate addition of ethenesulfonyl fluoride, as shown in Scheme 1. The compounds were purified to >95% purity by HPLC and their structure was confirmed by high-resolution MS and $^{1}H/^{13}C$ NMR spectroscopy. Representative examples are shown in Scheme 4 and Table 2.

Scheme 4. Representative antagonist compounds having SuFEx warhead.

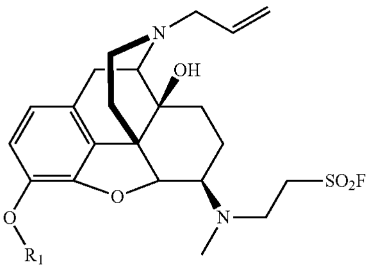

TJ-3,343

-continued

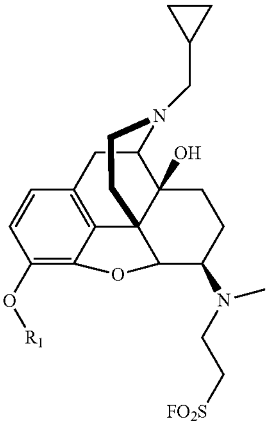

2a-x

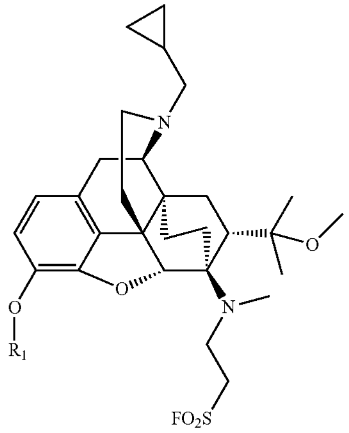

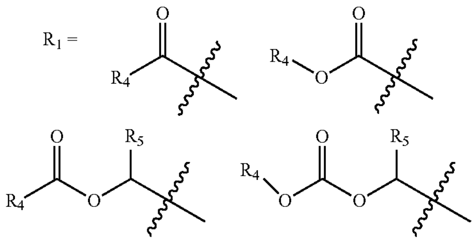

$R_4$ = —$CH_3$, —$C_2H_5$, t-butyl, —$CH_2$—$N(CH_3)_2$ $R_5$ = H or $CH_3$

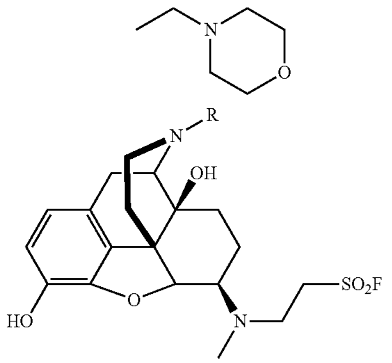

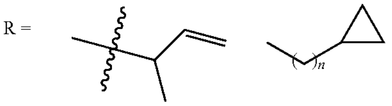

-continued
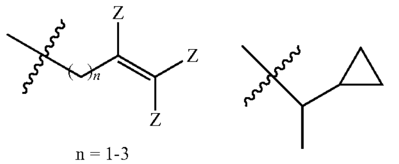
n = 1-3
Z = H, $CH_3$, F or $CF_3$
R =
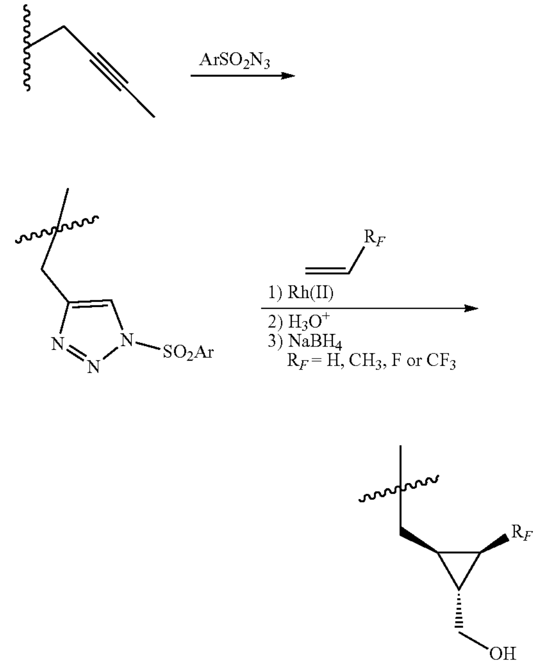
TABLE 2
| Representative sets of compounds having a SuFEx warhead. | |
|---|---|
| 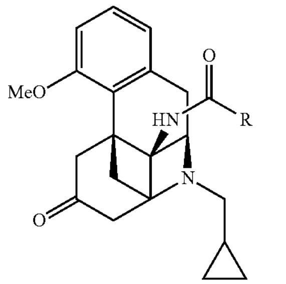 | 5 |
| 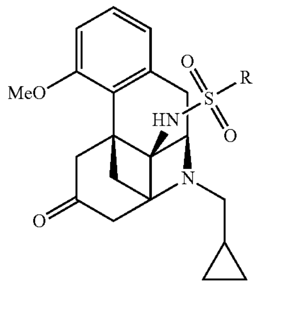 | 6 |
TABLE 2-continued
| Representative sets of compounds having a SuFEx warhead. | |
|---|---|
| 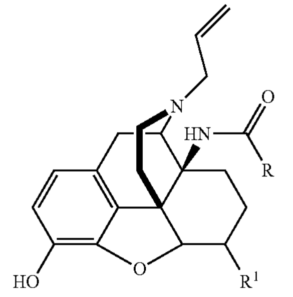 | 7 |
| 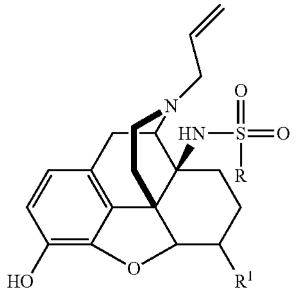 | 8 |
| 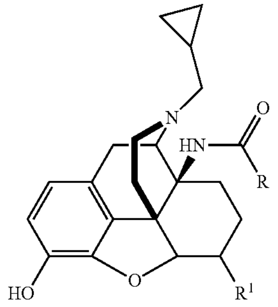 | 9 |
| 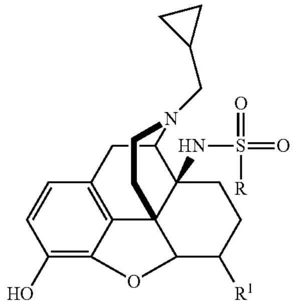 | 10 |
R =
| | |
|---|---|
| 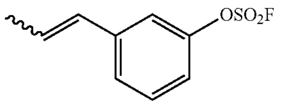 | 5a-10a |
| 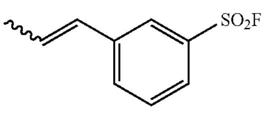 | 5b-10b |
| 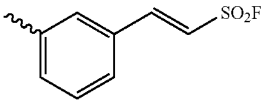 | 5c-10c |

TABLE 2-continued
| Representative sets of compounds having a SuFEx warhead. | |
|---|---|
| 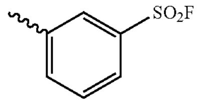 | 5d-10d |
| 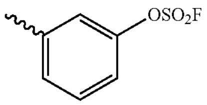 | 5e-10e |
| 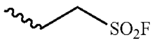 | 5f-10f |
| 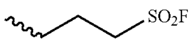 | 5g-10g |
| 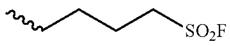 | 5h-10h |
| 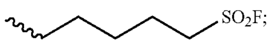 | 5i-10i |
and
$R^1$ is as defined in this Example or as defined for a formula described herein.
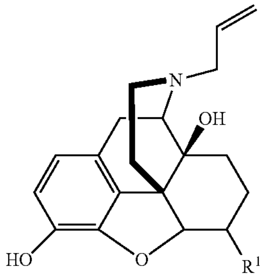
where $R^1$ is as defined herein or as shown in the structures below.
1a (TJ-345)
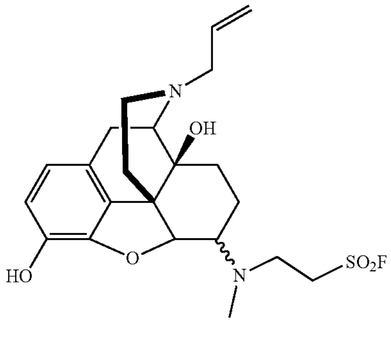
-continued
1b (TJ-3-343)
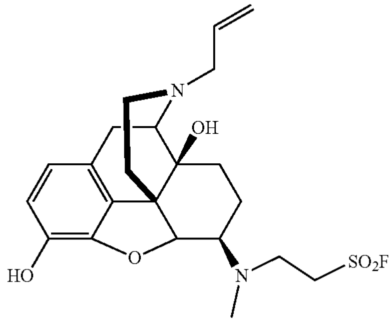
1c (TJ-4-485)
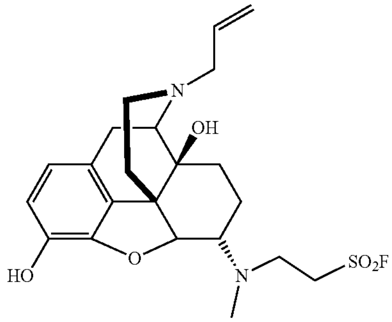
1d
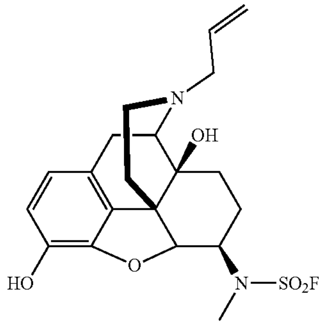
1e
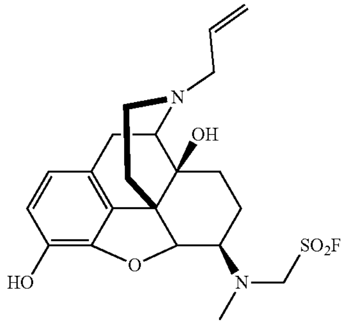
1f
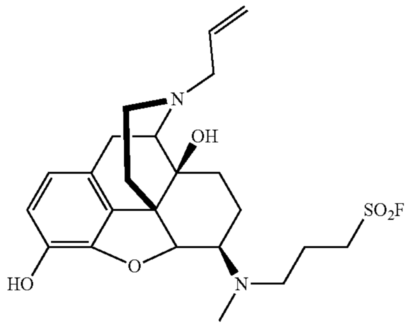

-continued
1g
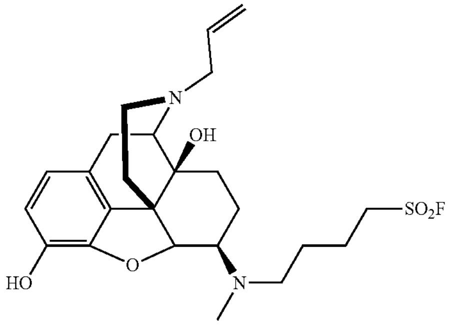
1h
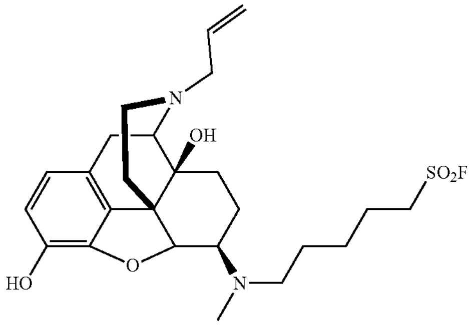
1i
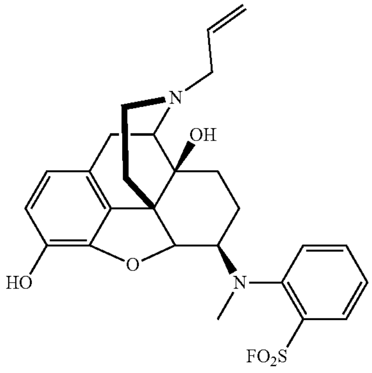
1j
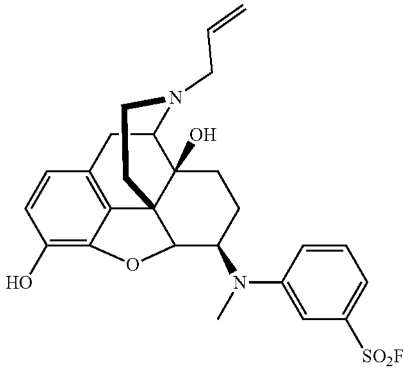
-continued
1k
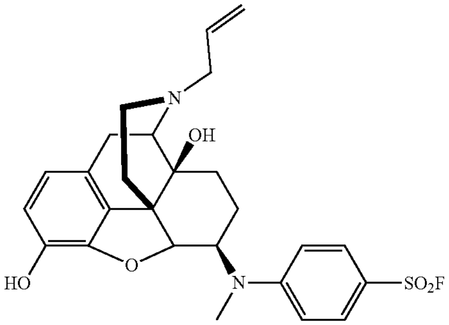
1l
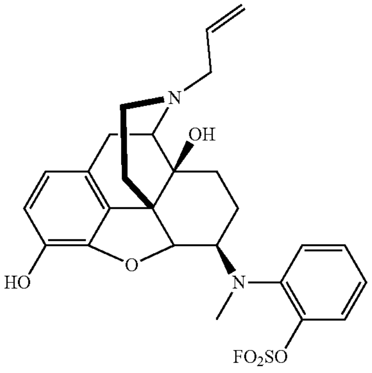
1m
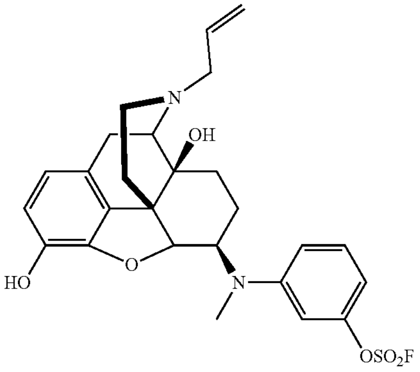
1n
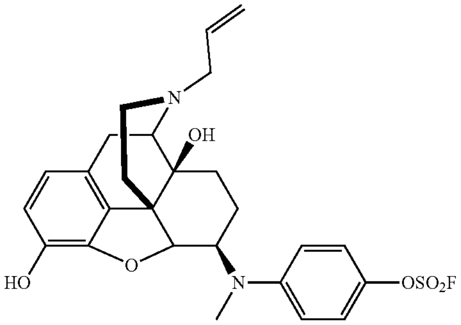

-continued
1o
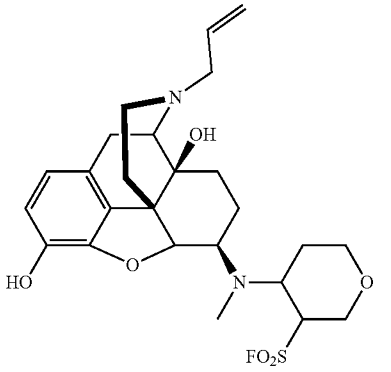
1p
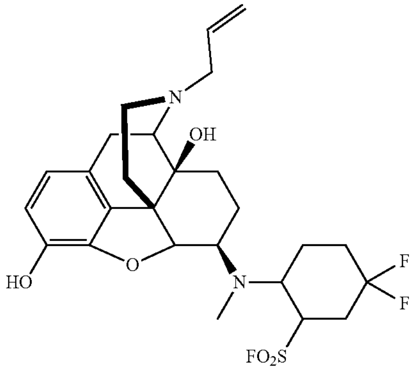
1q
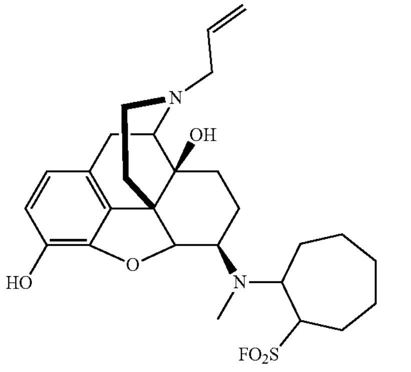
1r
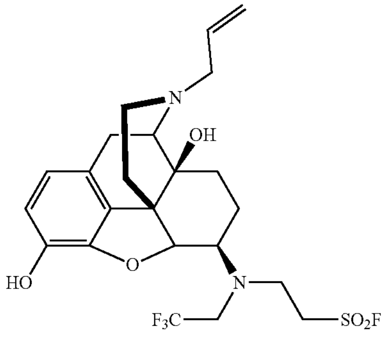
-continued
1s
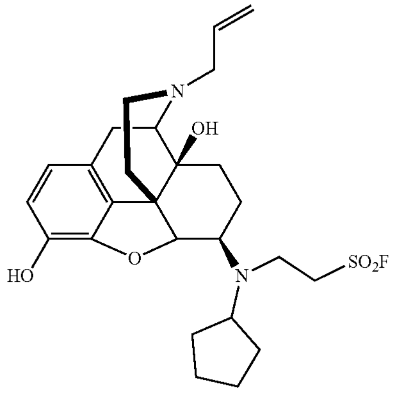
1t
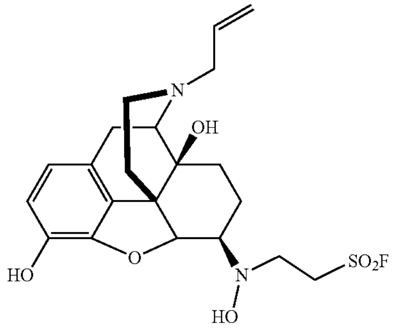
1u
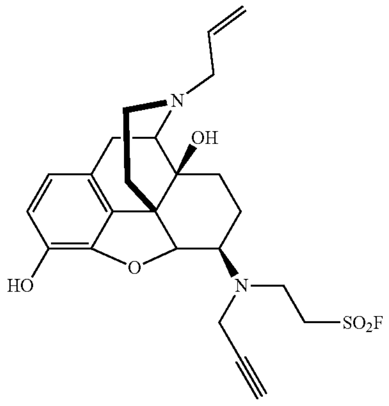
1v
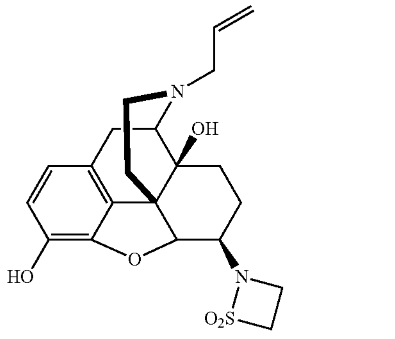

-continued

1w

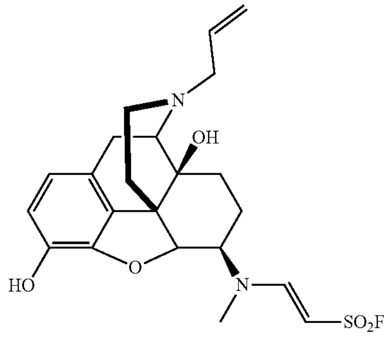

1x

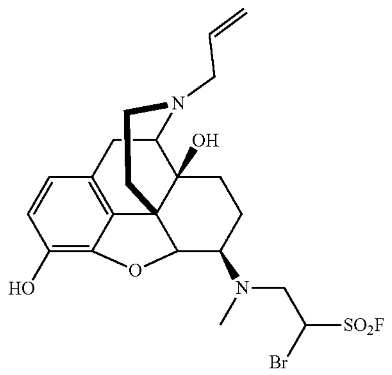

1n2

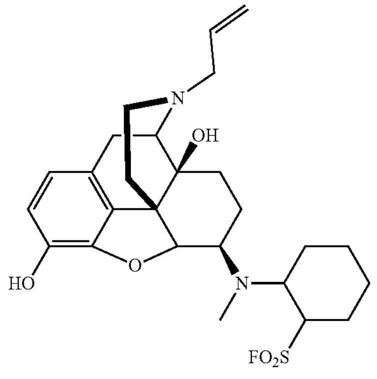

Additional compounds of the invention include the following formulas wherein $R^1$ is as shown for the structures above.

2a-x

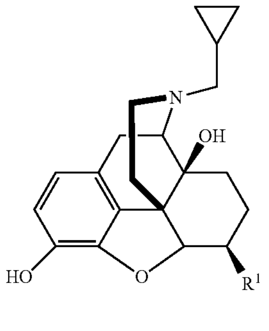

-continued 3a-x

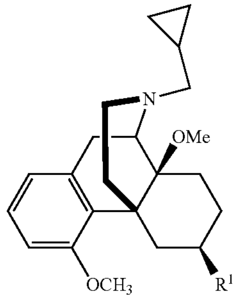

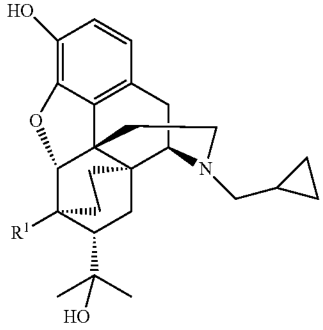

General Synthetic Methods

The invention also relates to methods of making the compounds and compositions of the compounds. The compounds and compositions can be prepared by any of the applicable techniques of organic synthesis, for example, the techniques described herein. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5$^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999); for heterocyclic synthesis see Hermanson, Greg T., Bioconjugate Techniques, Third Edition, Academic Press, 2013. A number of methods for the preparation of compounds are provided in the Examples below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 1 day. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g., inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e., routes or methods to prepare the compounds by the methods described herein or by methods well-known to those of skill in the art. The decision as to which groups to protect, when to do so, and the nature of the chemical protecting group "PG" will largely be dependent upon the chemistry of the reaction to be protected against (e.g., acidic, basic, oxidative, reductive or other conditions) and the intended direction of the synthesis.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard shell or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of about 0.01 mg/kg to about 100 mg/kg, about 0.05 mg/kg to about 60 mg/kg, about 0.1 mg/kg to about 50 mg/kg, about 0.1 mg/kg to about 35 mg/kg, about 0.5 mg/kg to about 35 mg/kg, or about 0.5 mg/kg to about 30 mg/kg of body weight per day. In some embodiments, a suitable dose will be in the range of about 0.05 mg/kg to about 45 mg/kg, about 0.1 mg/kg to about 30 mg/kg, about 0.1 mg/kg to about 10 mg/kg, about 0.1 mg/kg to about 5 mg/kg, about 0.5 mg/kg to about 5 mg/kg, about 1 mg/kg to about 5 mg/kg, or about 2-3 mg/kg of body weight per day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 $mg/m^2$, conveniently 10 to 750 $mg/m^2$, most conveniently, 50 to 500 $mg/m^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator.

The compounds described herein can be effective opioid antagonists and have higher potency and/or reduced toxicity as compared to corresponding antagonists that do not have the $SO_2F$ moiety. Preferably, compounds of the invention are more potent and less toxic than said corresponding antagonists, and/or have a different metabolic profile than said corresponding antagonists.

The invention provides therapeutic methods of treating opioid overdoses in a mammal, which involve administering to a mammal having an overdose an effective amount of a compound or composition described herein. A mammal includes a primate, human, rodent, canine, feline, bovine, ovine, equine, swine, caprine, bovine and the like. The ability of a compound of the invention to treat overdoses may be determined by using assays well known to the art.

The following Example is intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Preparation of TJ-345 and TJ-171

Synthesis of 6-α-N-methylnaltrexamine and 6-β-N-methylnaltrexamine

Synthesis of 6-α-N-methylnaltrexamine (3c) and 6-β-N-ethylnaltrexamine was performed according to a modified version of previously reported procedure (Mohamed et al., *J. Med. Chem.* 1986, 29(8), 1551-1553). To a mixture of naloxone (2 g, 5.8 mmol) and methylamine (2.0 M solution in methanol, 30 mL, 58.0 mmol) was added methanolic solution of $NaCNBH_3$ (240 mg, 3.6 mmol). The pH was adjusted to 7 with concentrated HCl. The mixture was then stirred at room temperature for 3 days. The solution was acidified to pH 9 with sodium carbonate, extracted with $CH_2Cl_2$, dried over $Na_2SO_4$, filtered and $CH_2Cl_2$ was removed in vacuo. The resultant crude product was purified by flash chromatography ($CH_3CN/MeOH/NH_4OH$, 7.5:2:0.5, v:v) to give the a diastereomer, 6-α-N-methylnaltrexamine (750 mg) and the 6-β-N-methylnaltrexamine (710 mg) as white solids.

Synthesis of TJ-345.

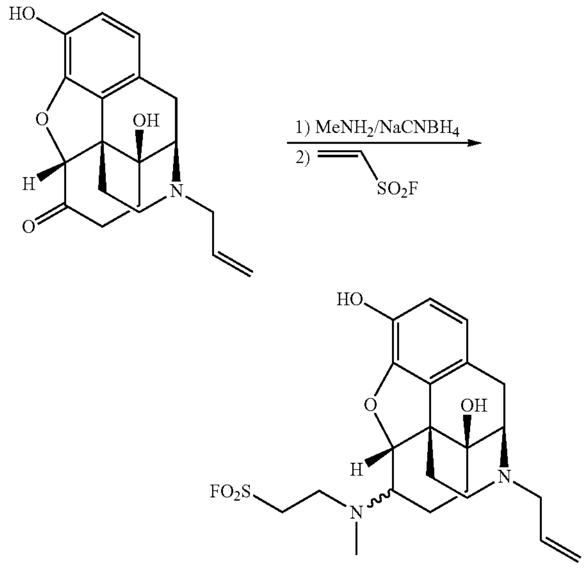

TJ-345
Mixure of isomers

A 1:1 mixture of 6-β-N-methylnaloxoneamine and 6-α-N-methylnaltrexamine (250 mg, 0.73 mmol) was dissolved in $CHCl_3$ (3 mL) and ethenesulfonyl fluoride (89 mg, 0.8 mmol) in 1 mL of $CHCl_3$ was added to this solution. The solution was stirred for 1 h at room temperature and concentrated to dryness. The crude product was washed with pentane (3 mL) to remove traces of ethenesulfonyl fluoride to afford TJ-345 (280 mg, 85% yield) as an off-white solid.

$^1$H NMR (600 MHz, Chloroform-d) δ 6.65 (d, J=8.0 Hz, 1H), 6.63 (d, J=8.1 Hz, 1H), 6.51 (d, J=8.1 Hz, 1H), 6.46 (d, J=8.2 Hz, 1H), 5.78-5.68 (m, 2H), 5.18-5.07 (m, 4H), 4.69 (dd, J=3.8, 1.6 Hz, 1H), 4.51 (d, J=7.9 Hz, 1H), 3.60-3.44 (m, 4H), 3.41-3.19 (m, 2H), 3.11-2.91 (m, 8H), 2.89-2.81 (m, 2H), 2.54-2.36 (m, 6H), 2.42 (s, 3H), 2.34 (s, 3H), 2.26-1.96 (m, 4H), 1.85-1.66 (m, 2H), 1.57-0.92 (m, 10H); $^{13}$C NMR (151 MHz, $cdcl_3$) δ 145.5, 142.2, 140.0, 137.5, 135.5, 135.2, 130.8, 131.7, 125.7, 124.7, 119.2, 118.2, 118.0, 117.6, 117.4, 92.2, 90.4, 70.5, 69.9, 64.3, 62.7, 62.5, 59.2, 57.8, 58.1, 50.1, 49.8, 49.2, 47.8, 47.9, 47.2, 43.8, 42.9, 40.8, 37.3, 33.8, 30.6, 30.3, 23.0, 22.9, 19.5, 16.2; $^{19}$F NMR (564 MHz, $CDCl_3$) δ 58.5, 57.4; HRMS (m/z): $[M+H]^+$ calcd for $C_{22}H_{30}FN_2O_5S$: 453.1859; found 453.1852.

Synthesis of TJ-4-171.

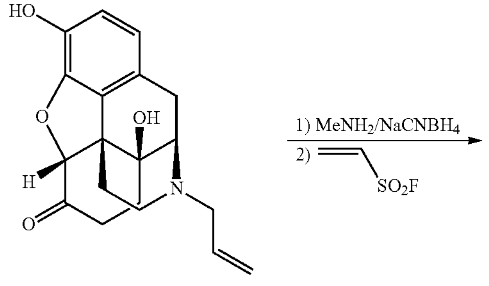

-continued

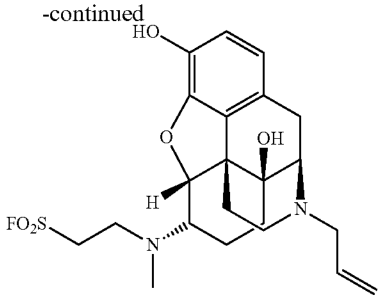

TJ-4-171
6-β ethyl isomer

6-β-N-Methylnaloxoneamine (1 g, 2.92 mmol) was dissolved in $CHCl_3$ (10 mL) and ethenesulfonyl fluoride (354 mg, 3.2 mmol) in 3 mL of $CHCl_3$ was added to this. The solution was stirred for 1 h at room temperature and concentrated to dryness. The crude product was washed with pentane (10 mL) to remove traces of ethenesulfonyl fluoride to afford TJ-171 (1.26 g, 94% yield) as an off white solid.

$^1$H NMR (600 MHz, Chloroform-d) δ 6.65 (d, J=8.0 Hz, 1H), 6.51 (d, J=8.1 Hz, 1H), 5.71 (ddt, J=16.7, 10.2, 6.4 Hz, 1H), 5.18-5.04 (m, 2H), 4.51 (d, J=7.9 Hz, 1H), 3.60-3.43 (m, 2H), 3.30-3.19 (m, 1H), 3.11-2.92 (m, 4H), 2.81 (d, J=5.6 Hz, 1H), 2.54-2.38 (m, 3H), 2.34 (s, 3H), 2.18-1.97 (m, 2H), 1.85 (qd, J=13.1, 2.8 Hz, 1H), 1.54 (dt, J=13.5, 3.3 Hz, 1H), 1.47-1.34 (m, 2H), 1.33-1.11 (m, 2H); $^{13}$C NMR (151 MHz, $cdcl_3$) δ 142.1, 139.9, 135.5, 131.7, 124.7, 119.2, 118.0, 117.3, 90.6, 70.5, 64.3, 62.7, 57.8, 49.8, 49.2, 47.8, 43.8, 37.3, 30.6, 30.6, 22.9, 19.5; $^{19}$F NMR (564 MHz, CDCl3) δ 58.5; HRMS (m/z): $[M+H]^+$ calcd for $C_{22}H_{30}FN_2O_5S$: 453.1859; found 453.1852.

Example 2. CLAMS In-Vivo Characterization

Figure 7:
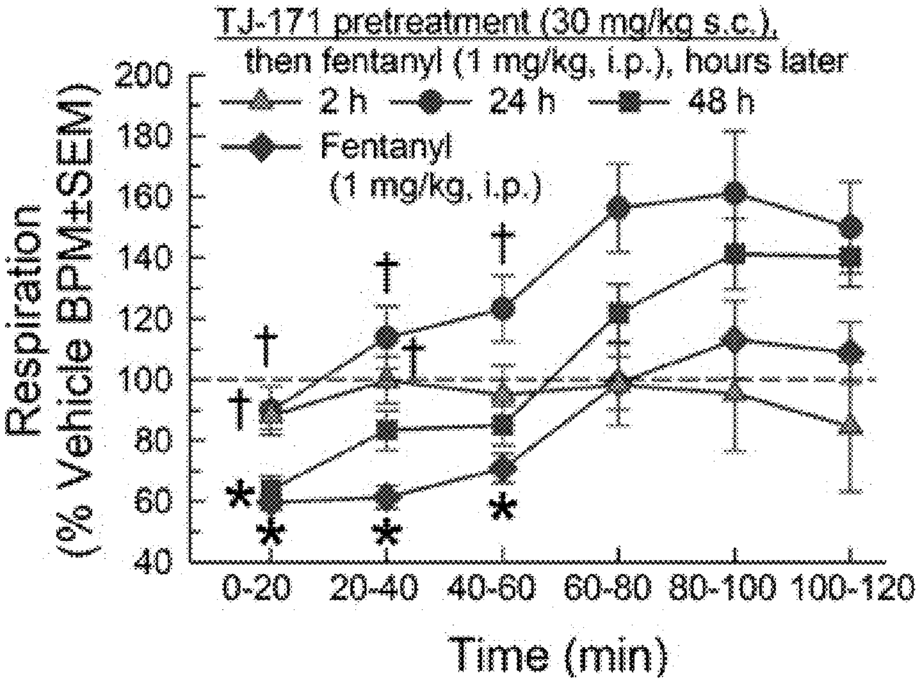
FIG. 7. Fentanyl (♦)-induced (A) respiratory depression and (B) ambulation is ameliorated by TJ-171 (30 mg/kg, s.c.) after a pretreatment of 2 h (▲) or 24 h (●) but not 48 h (■) in the CLAMS assay. *$p<0.05$ vs vehicle effect (dashed line); †$p<0.05$ vs fentanyl (1 mg/kg); 2-way REML ANOVA with Tukey's post hoc test. Points=12 mice/set (dashed line=normalized saline response, N=20 mice). (A) $F_{(20,305)}=4.97$, $p<0.0001$; (B) $F_{(20,303)}=15.16$, $p<0.0001$; time×treatment.
Figure 7:
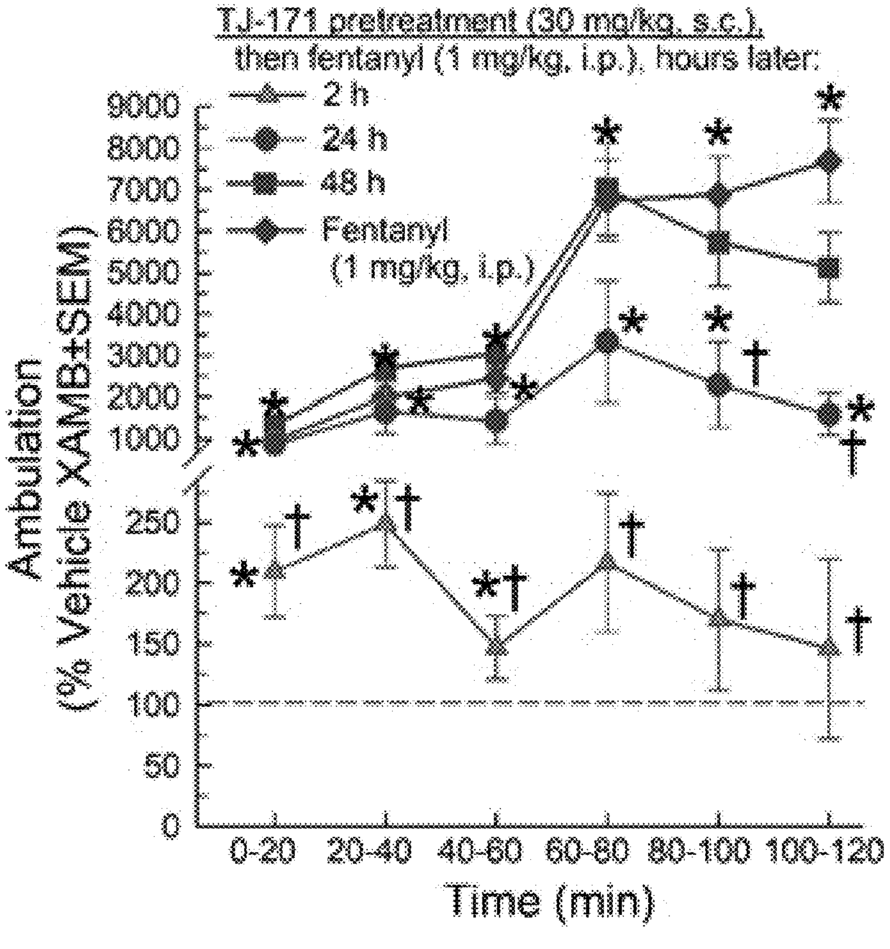

Compounds were assessed in reversing fentanyl-induced respiratory depression and ambulation in mice measured in the Comprehensive Lab Animal Monitoring System (CLAMS; FIG. 7). As expected, fentanyl induced significant time- and dose-dependent respiratory depression and hyper-ambulation. A 2-hour pretreatment with TJ-345 (30 mg/kg, s.c.) significantly reverses fentanyl-induced respiratory depression and hyperlocomotion. Importantly, the compound are efficacious after both i.c.v. or s.c. administration, indicating that TJ-345 has acceptable blood-brain barrier permeability. The data for TJ-171 (FIG. 7) demonstrates a fentanyl-protective effect and also that protection can last for at least 24 hours, while waning after 48 hours.

Improved properties of TJ-171 as a lead candidate. TJ-171 shows no evidence of opioid agonist effects. Doses of TJ-171 up to 30 mg/kg, s.c. show no antinociception in the mouse 55° C. tail-withdrawal assay.

TJ-171 shows prolonged MOR antagonism (▲, FIG. 4). TJ-171 (30 mg/kg, s.c.) produces prolonged MOR antagonism lasting at least 24 hours in the mouse 55° C. WWTW assay. This is an improvement over the same dose of TJ-345, which only partially antagonized morphine-induced antinociception at 24 hours.

TJ-171 demonstrates prolonged protection from fentanyl (FIG. 7). A single dose of TJ-171 (30 mg/kg, s.c.) protects for up to 24 hours against fentanyl-induced respiratory depression and hyperlocomotion in the CLAMS assay.

Figure 8:
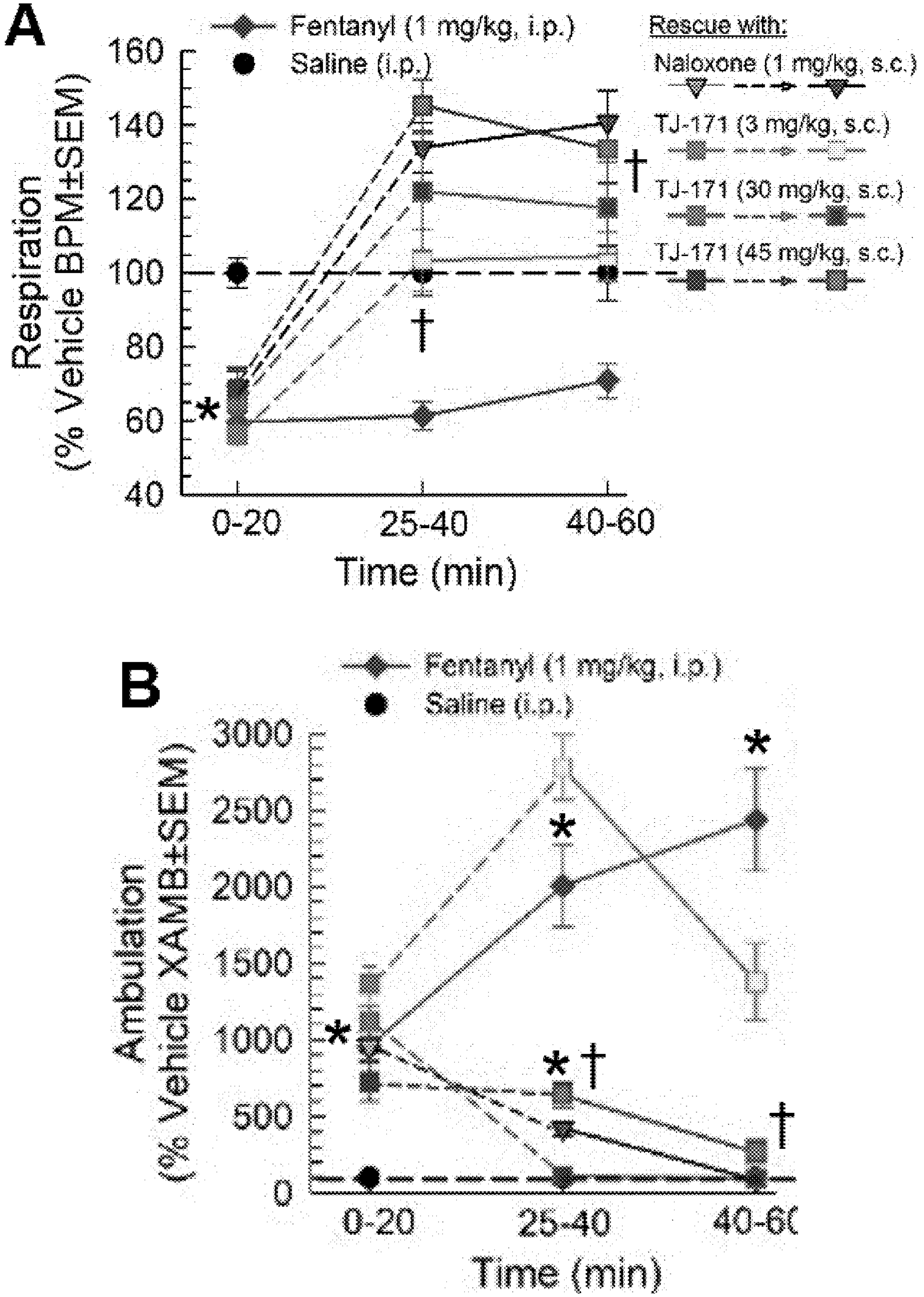
FIG. 8. Fentanyl (♦)-induced A: respiratory depression or B: ambulation is reversed by administration at 21 min of naloxone (▼) or TJ-171 (■, 3, 30 or 45 mg/kg, s.c.) in the CLAMS assay. *$p<0.05$ vs vehicle effect (dashed line); †$p<0.05$ vs fentanyl (1 mg/kg); 2-way REML ANOVA with Tukey's post hoc test. Points=6-12 mice/set (dashed line=normalized saline response, N=20 mice). 0-20 min: (A) $F_{(5,64)}=37.3$, $p<0.0001$; (B) $F_{(5,64)}=15.4$, $p<0.0001$ (1-way ANOVA). All: (A) $F_{(4.49,18.0)}=14.2$, $p<0.0001$; (B) $F_{(3.01,12.0)}=34.2$, $p<0.0001$; time×treatment.

TJ-171 rescues mice from fentanyl-induced respiratory depression (FIG. 8). After given fentanyl, mice demonstrated significant respiratory depression or hyperlocomotion (0-20 min, FIGS. 8A and 8B, respectively) within 20 minutes. Administration (at 21 minutes) of naloxone (1 mg/kg, s.c.) or TJ-171 (3-45 mg/kg, s.c.) swiftly reversed respiratory depression (FIG. 8A), whereas TJ-171 dose-dependently reversed hyperlocomotion after treatments of 30 or 45 mg/kg, s.c. (FIG. 8B).

Example 3. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

-continued

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

(I)

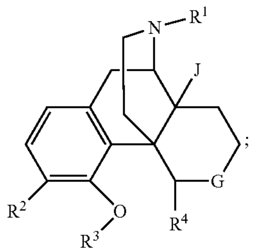

wherein

G is $CHNR^bR^c$, $CHR^x$, $CHOR^a$, or C═O;

$R^x$ is H or —$(C_1\text{-}C_8)$alkyl;

$R^a$ is H, —$(C_1\text{-}C_8)$alkyl, or —$(C_3\text{-}C_8)$cycloalkyl;

$R^b$ and $R^c$ are each independently —($C_1$-$C_8$)alkyl, H, —($C_3$-$C_8$)cycloalkyl, —C(═O)$R^d$, or —S(═O)$_2R^e$; or $R^b$ and $R^c$ taken together are —$CH_2$—$CH_2$—$SO_2$—;

$R^d$ and $R^e$ are each independently —($C_1$-$C_8$)alkyl, —($C_3$-$C_8$)cycloalkyl, or phenyl, wherein —($C_1$-$C_8$)alkyl, —($C_3$-$C_8$)cycloalkyl, or phenyl is substituted with —OS(═O)$_2$F, —S(═O)$_2$F, or unsaturated or saturated —($C_1$-$C_8$)alkyl-S(═O)$_2$F;

J is $OR^a$, H, or $NR^bR^c$, or J is a two-carbon alkyl bridge connected to the carbon atom of G and G is $CHNR^bR^c$, $CHR^x$, or $CHOR^a$;

$R^1$ is —($C_1$-$C_8$)alkyl, H, —($C_1$-$C_8$)alkyl($C_3$-$C_8$)cycloalkyl, —C(═O)$R^d$, or —S(═O)$_2R^e$;

$R^2$ is H, OH, $OR^f$, —($C_0$-$C_5$)C(═O)$R^f$, —($C_0$-$C_5$)C(═O)$OR^f$, —($C_0$-$C_5$)OC(═O)$OR^f$;

$R^f$ is —($C_1$-$C_8$)alkyl wherein —($C_1$-$C_8$)alkyl is optionally substituted with amine;

$R^3$ and $R^4$ taken together form a single bond; or $R^3$ is H, —($C_1$-$C_8$)alkyl, or —($C_3$-$C_8$)cycloalkyl; and $R^4$ is H;

wherein —($C_1$-$C_8$)alkyl is unsaturated or saturated and unbranched or branched, and at least of one of J or G comprises —S(═O)$_2$F.

2. The compound of claim 1 wherein the compound of Formula I is a compound of Formula II:

(II)

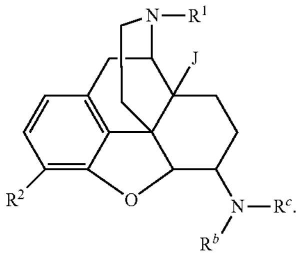

3. The compound of claim 1 wherein the compound of Formula I is a compound of Formula III:

(III)

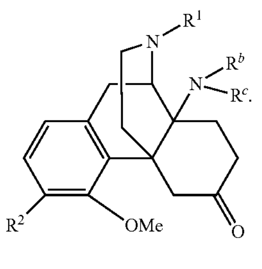

4. The compound of claim 1 wherein the compound is TJ-345:

(TJ-345)

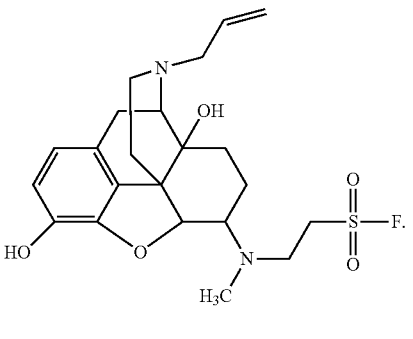 [SMILES: C=CCN1CCC23c4c5ccc(O)c4OC2C(N(C)CCS(=O)(=O)F)CCC3(O)C1C5]

5. A compound of Formula IIA:

(IIA)

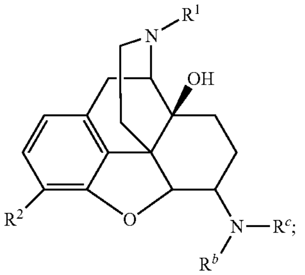

wherein $R^1$ is —($C_1$-$C_3$)alkyl-CZ═$CZ_2$ wherein Z is H, Me, or $CF_3$, —CH(Me)-CH═$CH_2$, —($C_1$-$C_3$)alkyl-cyclopropyl, —CH(Me)-cyclopropyl, propargyl, arylsulfonamide-substituted triazole, or —$CH_2$-cyclopropyl wherein the cyclopropyl is substituted with hydroxymethyl and $R^F$ wherein $R^F$ is H, Me, F, or $CF_3$;

$R^2$ is $OR^{10}$ wherein $R^{10}$ is H, —C(═O)$R^{11}$, —C(═O)$OR^{11}$, —$CH_2$O—C(═O)$R^{11}$, —CH(Me)-O—C(═O)$R^{11}$, —$CH_2$O—C(═O)$OR^{11}$, or —CH(Me)-O—C(═O)$OR^{11}$, and $R^{11}$ is unbranched or branched —($C_1$-$C_8$)alkyl, —$CH_2NH_2$, —$CH_2NMe_2$, or —$CH_2$—N-morpholinyl;

$R^b$ is H, Me, —$CH_2CF_3$, —OH, —($C_3$-$C_8$)cycloalkyl, or propargyl; and $R^c$ is —S(═O)$_2$F, —($C_1$-$C_8$)alkyl-S(═O)$_2$F wherein the alkyl is optionally further substituted with bromo or chloro, —CH═CH—S(═O)$_2$F, phenyl substituted with —S(═O)$_2$F, tetrahydropyran substituted with —S(═O)$_2$F, or —($C_3$-$C_8$)cycloalkyl substituted with —S(═O)$_2$F and optionally further substituted by two fluorine atoms on a ring carbon;

or $R^b$ and $R^c$ taken together are —$CH_2$—$CH_2$—$SO_2$—.

6. The compound of claim 5 wherein $R^1$ is allyl or —$CH_2$-cyclopropyl, and $R^2$ is OH.

7. A compound of Formula IIB:

(IIB)

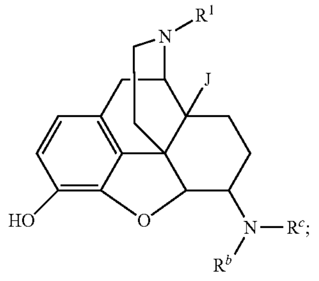

wherein $R^1$ is allyl or —$CH_2$-cyclopropyl;

J is OH or OMe;

$R^b$ is Me, —$CH_2CF_3$, —OH, —($C_3$-$C_8$)cycloalkyl, or propargyl; and $R^c$ is —S(═O)$_2$F, —($C_1$-$C_8$)alkyl-S(═O)$_2$F wherein the alkyl is optionally further substituted with bromo or chloro, —CH═CH—S(═O)$_2$F, phenyl substituted with —S(═O)$_2$F, tetrahydropyran substituted with —S(═O)$_2$F, or —($C_3$-$C_8$)cycloalkyl substituted with —S(═O)$_2$F and optionally further substituted by two fluorine atoms on a ring carbon;

or $R^b$ and $R^c$ taken together are —$CH_2$—$CH_2$—$SO_2$—.

8. The compound of claim 7 wherein the compound is:

1a (TJ-345)

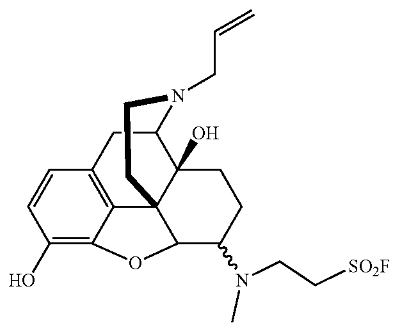

1b (TJ-3-343)

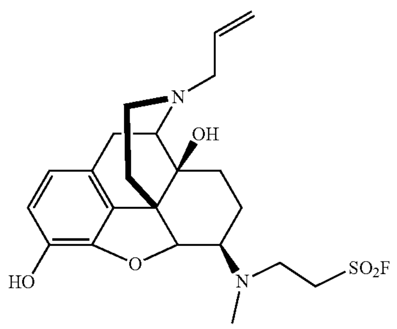

-continued 1c (TJ-4-485)

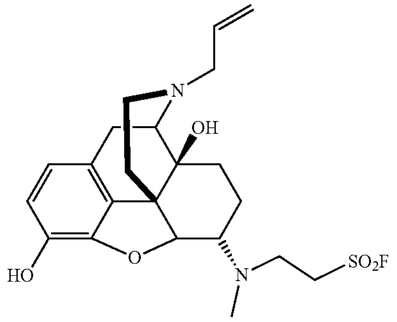

1d

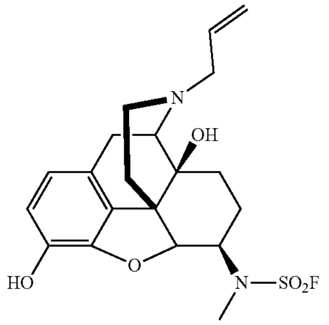

1e

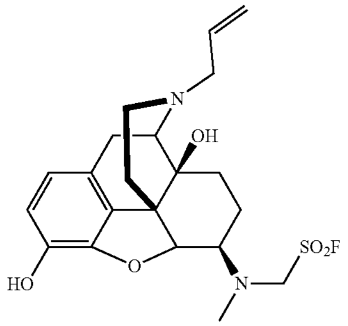

1f

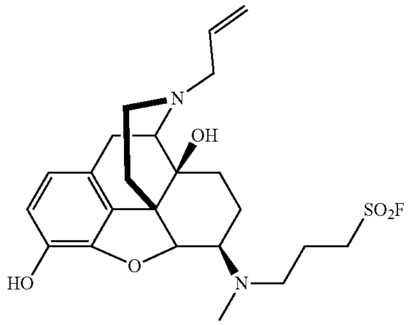

1g

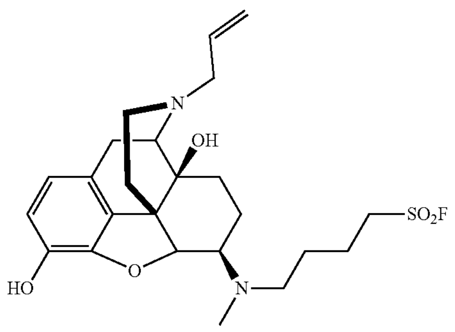

-continued
1h
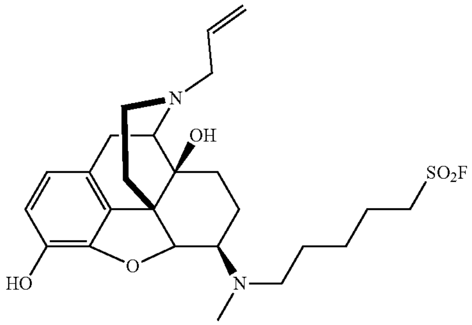
1i
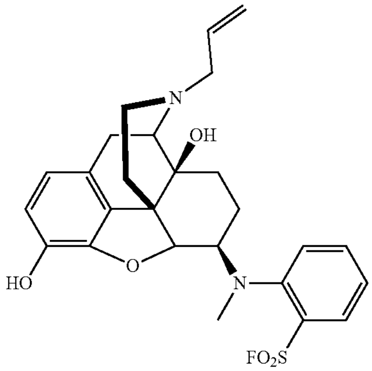
1j
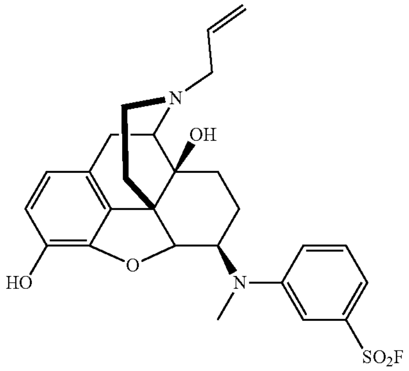
1k
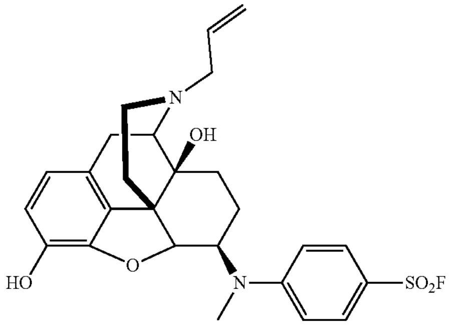
-continued
1n2
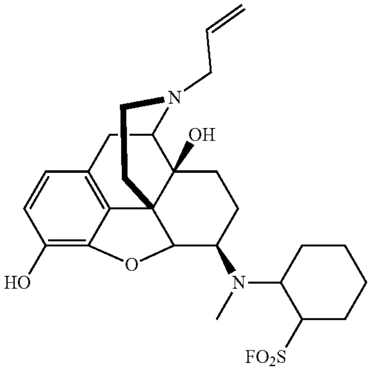
1o
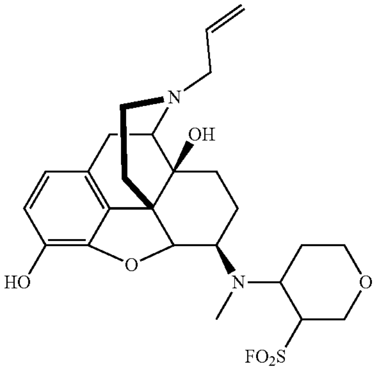
1p
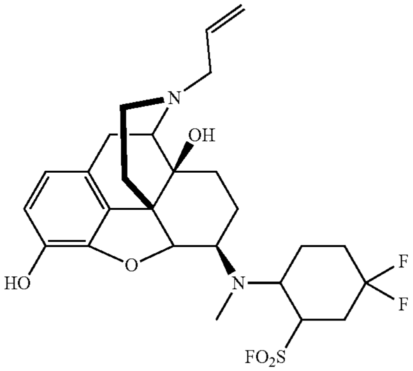
1q
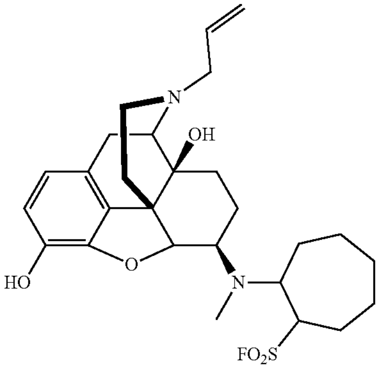

-continued

1r

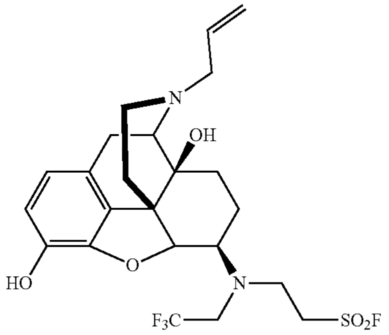

1s

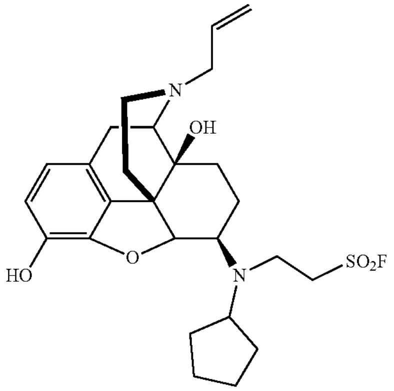

1t

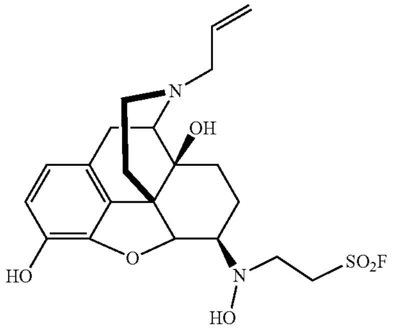

1u

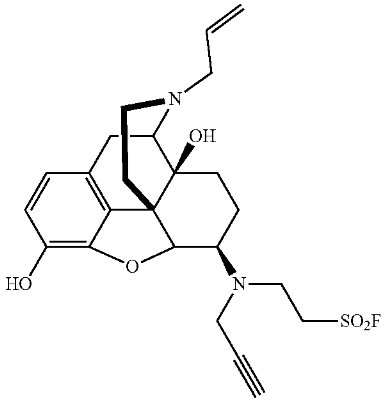

-continued

1v

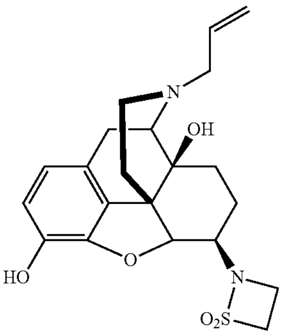

1w

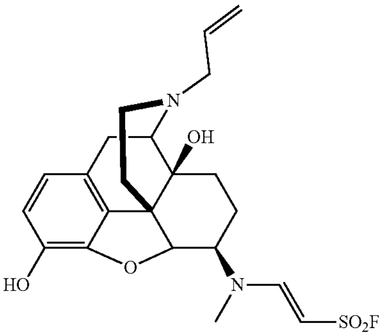

or

1x

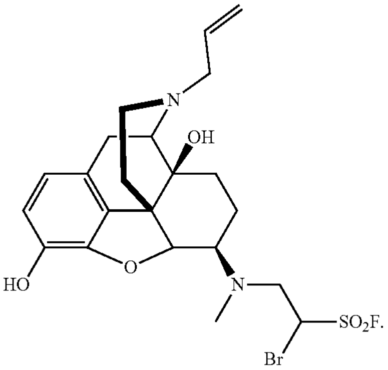

9. A compound of Formula IIC:

(IIC)

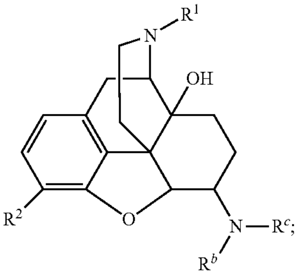

wherein $R^1$ —($C_1$-$C_3$)alkyl-CZ═$CZ_2$ wherein Z is H, Me, or $CF_3$, —CH(Me)-CH═$CH_2$, —($C_1$-$C_3$)alkyl-cyclopropyl, —CH(Me)-cyclopropyl, propargyl, arylsulfonamide-substituted triazole, —$CH_2$-cyclopropyl wherein the cyclopropyl is substituted with hydroxymethyl and $R^F$ wherein $R^F$ is H, Me, F, or $CF_3$, —($C_1$-$C_8$)alkyl-S(═O)$_2$F, phenyl substituted with —S(═O)$_2$F, phenyl substituted with $-OS(=O)_2F$, $-CH=CH$-Ph substituted with $-S(=O)_2F$, $-CH=CH$-Ph substituted with $-OS(=O)_2F$, or phenyl substituted with $-CH=CH-S(=O)_2F$;

$R^2$ is $OR^{10}$ wherein $R^{10}$ is H, $-C(=O)R^{11}$, $-C(=O)OR^{11}$, $-CH_2O-C(=O)R^{11}$, $-CH(Me)-O-C(=O)R^{11}$, $-CH_2O-C(=O)OR^{11}$, or $-CH(Me)-O-C(=O)OR^{11}$, and $R^{11}$ is unbranched or branched $-(C_1-C_8)$alkyl, $-CH_2NH_2$, $-CH_2NMe_2$, or $-CH_2-N$-morpholinyl;

$R^b$ is Me; and $R^c$ is $-(C_1-C_8)$alkyl-$S(=O)_2F$.

10. The compound of claim 9 wherein $R^1$ is allyl or $-CH_2$-cyclopropyl, and $R^2$ is OH.

11. A compound of Formula IIIA:

(IIIA)

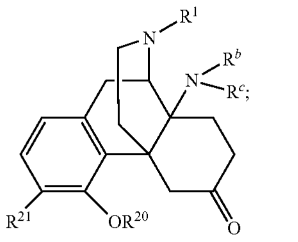

wherein $R^1$ is allyl or $-CH_2$-cyclopropyl;

$R^b$ is H;

$R^c$ is $-C(=O)-R^{12}$ or $-S(=O)_2-R^{13}$;

$R^{12}$ is $-(C_1-C_3)$alkyl-$CZ=CZ_2$ wherein Z is H, Me, or $CF_3$, $-CH(Me)-CH=CH_2$, $-(C_1-C_3)$alkyl-cyclopropyl, $-CH(Me)$-cyclopropyl, propargyl, arylsulfonamide-substituted triazole, $-CH_2$-cyclopropyl wherein the cyclopropyl is substituted with hydroxymethyl and $R^F$ wherein $R^F$ is H, Me, F, or $CF_3$, $-(C_1-C_8)$alkyl-$S(=O)_2F$, phenyl substituted with $-S(=O)_2F$, phenyl substituted with $-OS(=O)_2F$, $-CH=CH$-Ph substituted with $-S(=O)_2F$, $-CH=CH$-Ph substituted with $-OS(=O)_2F$, or phenyl substituted with $-CH=CH-S(=O)_2F$;

$R^{13}$ is $-(C_1-C_8)$alkyl-$S(=O)_2F$, phenyl substituted with $-S(=O)_2F$, phenyl substituted with $-OS(=O)_2F$, $-CH=CH$-Ph substituted with $-S(=O)_2F$, $-CH=CH$-Ph substituted with $-OS(=O)_2F$, or phenyl substituted with $-CH=CH-S(=O)_2F$;

$R^{20}$ is H or $-(C_1-C_8)$alkyl; and $R^{21}$ is H or $-C(=O)NH_2$.

12. A method to treat an opioid drug overdose comprising administering an effective amount of a mu-opioid antagonist to a subject in need thereof, wherein the antagonist is a compound of claim 1, wherein the antagonist covalently binds to a mu-opioid receptor of the subject via a sulfur (VI) fluoride group of the antagonist when the antagonist is in contact with the mu-opioid receptor, thereby treating the opioid drug overdose.

13. The method of claim 12 wherein the antagonist has a pharmacological duration of action in the subject at least twice the time of a corresponding a mu-opioid antagonist that does not comprise a sulfur (VI) fluoride group.

14. The method of claim 13 wherein treating the opioid drug overdose comprises reducing or alleviating opioid-induced respiratory depression.

15. The method of claim 13 wherein the antagonist is:

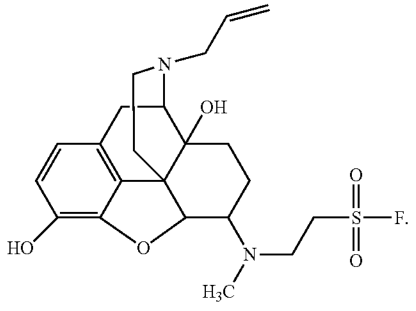 [SMILES: C=CCN1CCC23c4c5ccc(O)c4OC2C(N(C)CCS(=O)(=O)F)CCC3(O)C1C5]

16. A method to reduce or block the effect of opioid intoxication comprising administering an effective amount of a mu-opioid antagonist to a subject in need thereof, wherein the antagonist is a compound of claim 1, thereby reducing or blocking the effect of opioid intoxication.

17. The method of claim 16 wherein the opioid intoxication is intoxication caused by fentanyl or a derivative thereof.

18. The method of claim 17 wherein the antagonist is:

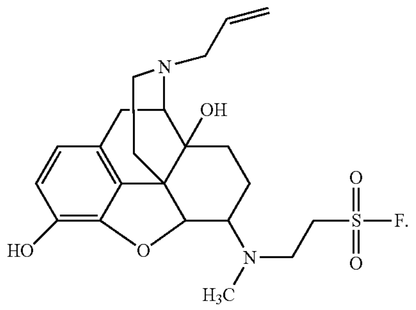

* * * * *